(12) United States Patent
Ferris et al.

(10) Patent No.: US 7,343,194 B2
(45) Date of Patent: Mar. 11, 2008

(54) METHOD AND APPARATUS FOR PERFORMING NEUROIMAGING

(75) Inventors: Craig F. Ferris, Holden, MA (US); Arthur C. Allard, Templeton, MA (US); Reinhold Ludwig, Paxton, MA (US); Gene Bogdanov, Manchester, CT (US)

(73) Assignee: Insight Neuroimaging Systems, LLC, Worcester, MA (US)

( * ) Notice: Subject to any disclaimer, the term of this patent is extended or adjusted under 35 U.S.C. 154(b) by 967 days.

(21) Appl. No.: 10/409,625

(22) Filed: Apr. 8, 2003

(65) Prior Publication Data

US 2004/0204642 A1 Oct. 14, 2004

(51) Int. Cl.
*A61B 5/05* (2006.01)

(52) U.S. Cl. .............. 600/415; 600/407; 600/411

(58) Field of Classification Search .......... 600/410, 600/421, 415, 422, 417, 407, 411; 324/309; 606/130

See application file for complete search history.

(56) References Cited

U.S. PATENT DOCUMENTS

| | | | | |
|---|---|---|---|---|
| 5,349,956 A * | 9/1994 | Bonutti | .............. | 600/425 |
| 5,724,970 A * | 3/1998 | Votruba et al. | .............. | 600/415 |
| 5,810,006 A * | 9/1998 | Votruba et al. | .............. | 600/415 |
| 6,275,723 B1 * | 8/2001 | Ferris et al. | .............. | 600/417 |
| 6,778,849 B1 * | 8/2004 | Ninomiya et al. | .............. | 600/422 |
| 2001/0053878 A1 * | 12/2001 | Ferris et al. | .............. | 600/415 |
| 2002/0077539 A1 * | 6/2002 | Schmit et al. | .............. | 600/410 |
| 2002/0193683 A1 * | 12/2002 | Danielsson et al. | .............. | 600/411 |
| 2004/0220467 A1 * | 11/2004 | Bonutti | .............. | 600/407 |

* cited by examiner

*Primary Examiner*—Brian L. Casler
*Assistant Examiner*—Joel Lamprecht
(74) *Attorney, Agent, or Firm*—Darby & Darby P.C.

(57) ABSTRACT

In one aspect, a restraining assembly for an awake animal within a magnetic resonance imaging (MRI) device is provided and includes a body restrainer having a first part and a second part that hold a body of the awake animal therebetween. The assembly is of a dual coil design in that it has a volume coil for generating an excitation RF signal and an RF surface coil for receiving an RF response from the animal. The assembly further includes components that serve to restrain movements of the animal, thereby eliminating motion artifacts during the MRI procedure. For example, the assembly preferably includes an adjustable hip holder that has a first section that seats against and applies a restraining force to a buttocks/hip area of the animal and a second section that is adjustably coupled to a pivoting member that is attached to the first section of the body restrainer such that the hip holder is adjustable in both a longitudinal direction along a length of the body restrainer and an up/down direction within the body restrainer between the first and second parts thereof. The pivoting member having features that permit the hip holder to be locked in a desired location so that a sufficient restraining force is applied the animal.

30 Claims, 24 Drawing Sheets

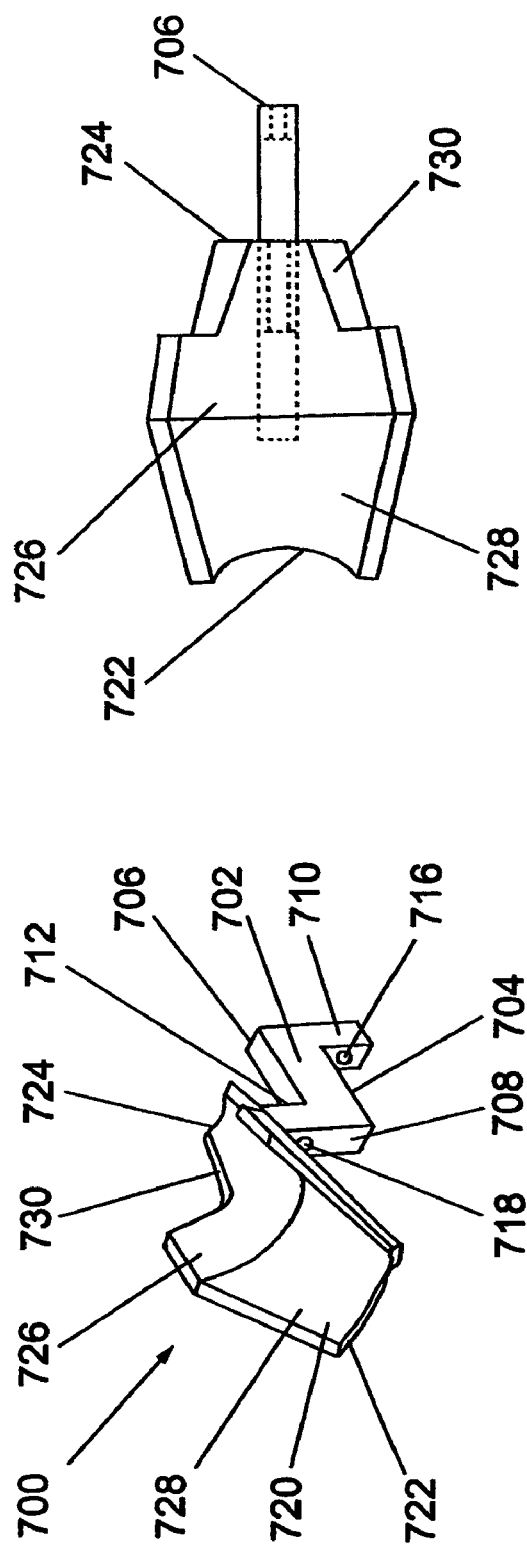
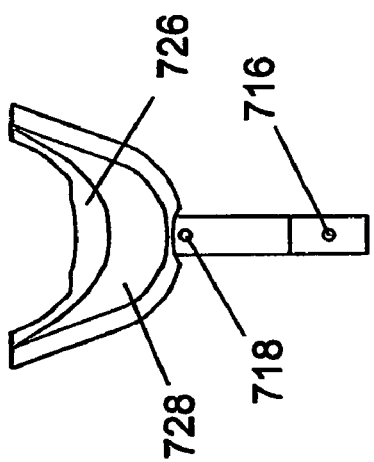
Fig. 18
Fig. 19
Fig. 17

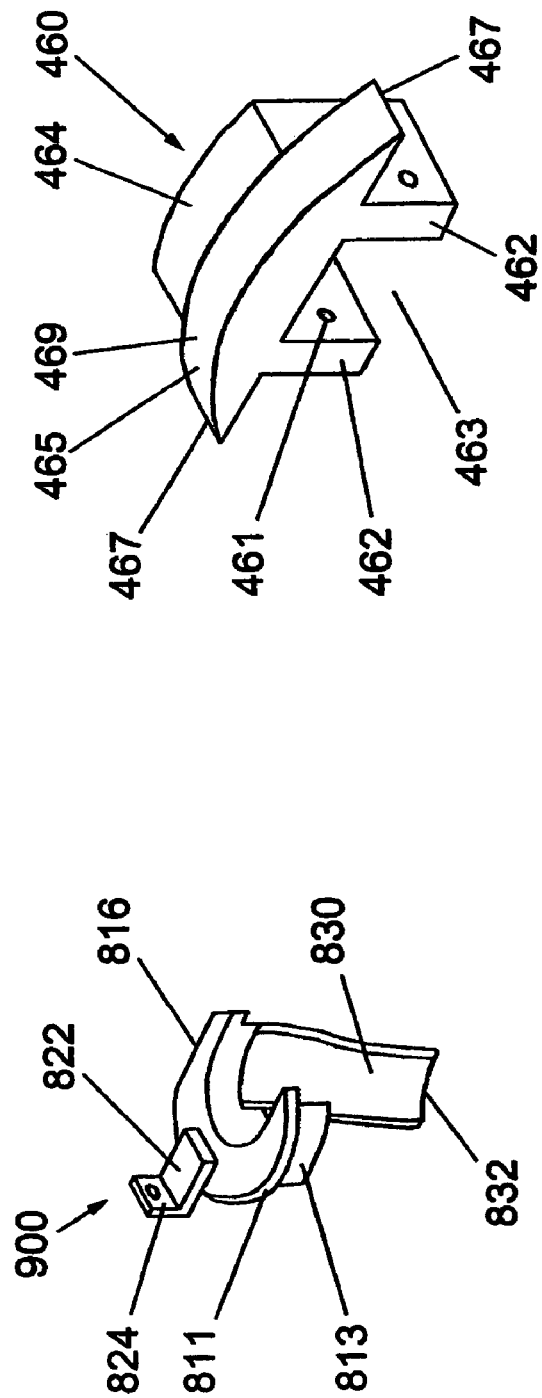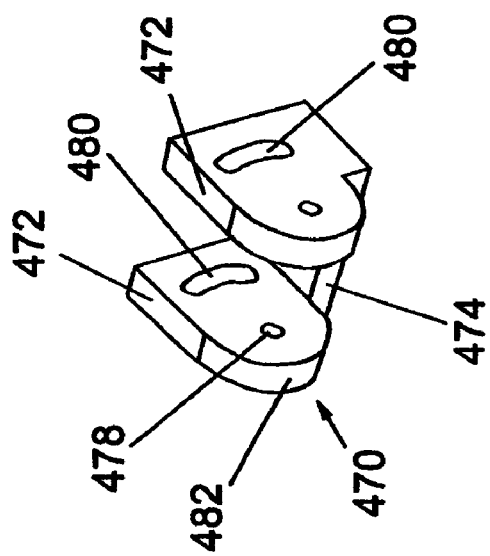

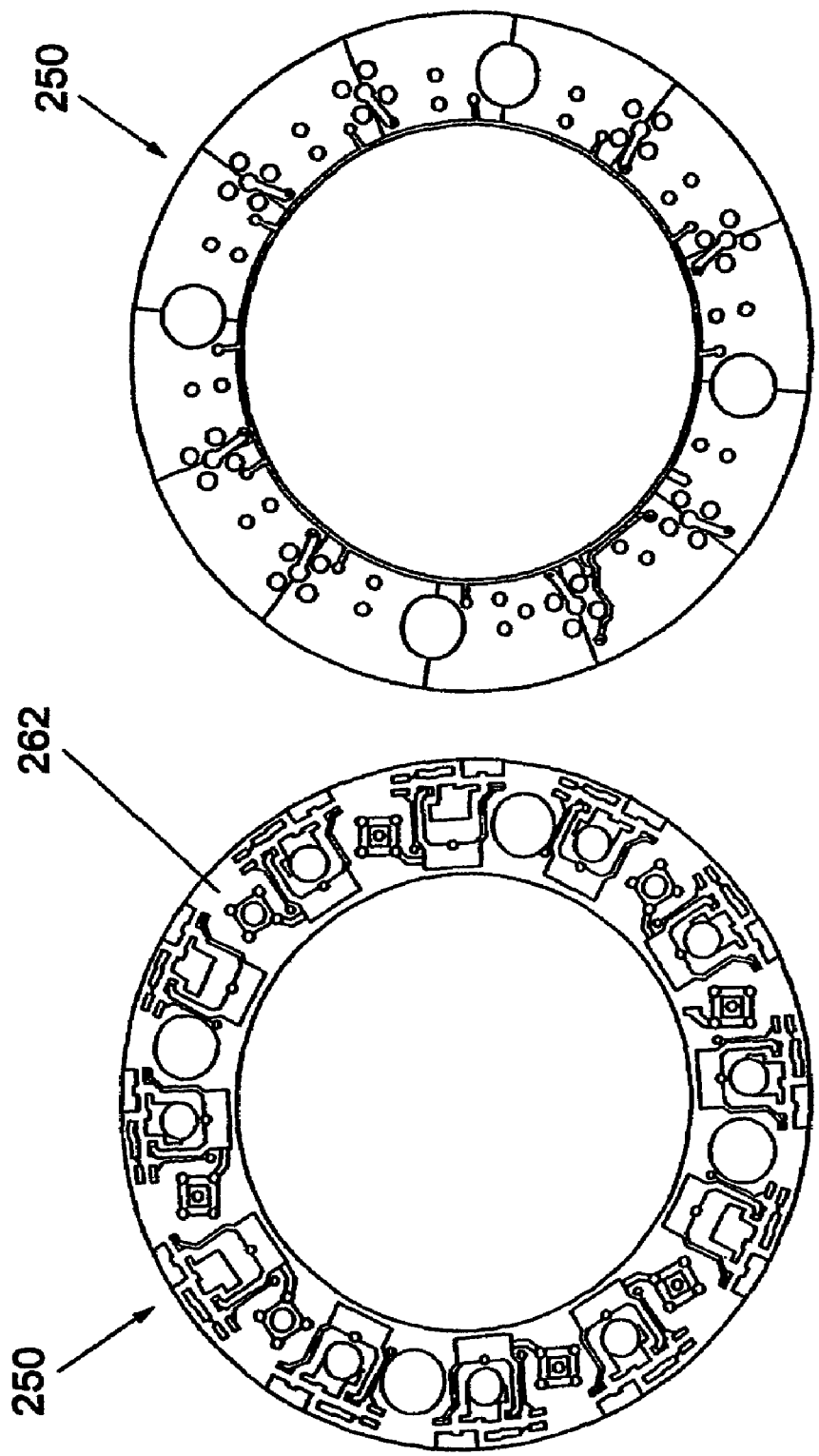

METHOD AND APPARATUS FOR PERFORMING NEUROIMAGING

GOVERNMENT SUPPORT

The invention was supported, in whole or in part, a grant number R42DA13867 from National Institute on Drug Abuse. The Government has certain rights in the invention.

TECHNICAL FIELD

The present invention relates to magnetic resonance imaging, and more particularly to a method and apparatus for performing functional magnetic resonance imaging (fMRI) in conscious animals.

BACKGROUND

Human studies utilizing fMRI have advanced our understanding of the regional and functional interplay between populations of neurons serving sensory, integrative and motor functions. Changes in neuronal activity are accompanied by specific changes in hemodynamics such as cerebral blood flow, cerebral blood volume, and blood oxygenation. Functional MRI has been used to detect these changes in response to visual stimulation, somatosensory activation, motor tasks, and emotional and cognitive activity. When the brain is activated by any of these conditions, the blood flow and delivery of oxygen to the active regions, the tissue oxygen uptake resulting in an increase in blood oxy-hemoglobin ($HbO_2$) content. The susceptibility difference between diamagnetic oxy-hemoglobin and paramagnetic deoxy-hemoglobin (Hb) creates local magnetic field distortions that affect the processional frequency of the water protons. The consequential change in magnetic resonance (MR) signal intensity which is proportional to the ratio of $HbO_2$ to Hb. These signal-intensity alterations related to blood oxygenation are termed the BOLD (blood oxygenation-level-dependent) effect. The voxels in paramagnetic Hb content that decreases are illuminated in the image.

While most work on fMRI has been done in humans, it has been difficult to use this technology in conscious animals because of motion artifact. As a result, most studies to date have been limited to animals which are typically anesthetized in order to minimize this problem of motion artifacts. The low level of arousal during anesthesia either partially or completely suppresses the fMRI response and has impeded fMRI application to the more physiologically relevant functions that have been noted in humans.

Since image resolution is a salient feature of fMRI, precautions to ensure improved image quality with minimized head movements are essential. In addition to head movement, it has been observed that any motion outside the field of view can obscure or mimic changes in signal.

Another, equally significant component for achieving high temporal and spatial image resolution is the generation of radiofrequency (RF) magnetic fields. The RF field pulses are transmitted to flip protons into the transverse plane of the main direct current (DC) magnetic field. As these protons process and relax back into the longitudinal plane of the main magnetic field they emit RF magnetic field signals. The electrical assemblies capable of sending and receiving RF signals are called RF probes, coils, or resonators. Ideally, a RF coil used for magnetic field transmission creates a large homogenous area of proton activation at a very narrow bandwidth center around the proton resonance frequency with minimal power requirements. An RF coil used for receiving covers the largest region of interest within the sample at the highest signal-to-noise ratio (SNR). RF coils are either volume coils or surface coils. A volume coil has the advantage of both sending and receiving RF signals from large areas of the sample. However, signal-to-noise ratio is compromised because a large spatial domain contributes to the RF signal, resulting in additional noise and thereby obscuring the RF signal from the region of interest. A surface coil has the advantage of improved SNR due to its close proximity to the sample. Unfortunately, a surface coil is ill suited for RF energy transmission owing to the fact that only a small proton area can be activated. Two criteria are sought in the design of superior coil performance for high field animal studies. First, the coils must be as efficient as possible. Transmission efficiency is increased by reducing the resistive coil losses through appropriate arrangement of conductors, the use of a shield, and the employment of low loss dialectric materials. By using a separate surface coil in proximity over the desired field of view (FOV) or region of interest, the reception efficiency of the acquired NMR signal is further increased. In imaging, spatial and temporal resolutions are proportional to SNR.

The second criterion to be met for a volume coil, is the uniformity or homogeneity over a desired FOV in the animal sample. To achieve both homogeneity and efficiency for volume coils of Larmor wavelength dimensions, further improvements are required. Conventional state-of-the-art so called birdcage coil designs will be less efficient at these currents.

So-called transversal electromagnetic (TEM) resonator designs have already shown promise for high-frequency, large volume coil applications for humans. However, these TEM designs must be modified for animal application and for the highest frequency allowed by present and future magnets, e.g.; for the 9.4T, and the 11.74T, magnets presently being built for laboratory animal studies.

Increased SNR is sought by malting NMR measurements at higher magnetic, or Bo, fields. Main magnetic field strength is, however, only one of several parameters affecting the MR sensitivity. RF coil and tissue losses can significantly limit the potential SNR gains realized at high fields. SNR (and reciprocal transmission efficiency) will suffer when the coil's ohmic resistance, radiation resistance, coupled tissue losses, RF magnetic field and angular frequency are not optimized.

Tissue losses increasingly impact SNR at higher frequencies. These conductive and dielectric losses represented are limited in practice by using local surface coils, or volume coils efficiently coupled to a region of interest. In addition to tissue loading, RF losses in the coils themselves become significant at higher frequencies. The RF coil loss increases with frequency as do the resistive losses in the coil RC (resonance circuit), which increases with the square root of the angular frequency, and the losses from radiation resistance, which increases as at the fourth power of the angular frequency. The radiation losses also increase as the coil size increases as $S^2$, where S is the area bounded by the coil.

From the above, it is apparent that radiative losses to the sample and environment, as well as conductive losses to the load of a coil become severe to the point of limiting and eventually degrading the SNR gains otherwise expected at higher magnetic field strengths. Physically, as a coil is increased in dimension and/or frequency, its equivalent electrical circuit length increases, the coil ceases to behave like a conventional coil (RF field storage circuit) and begins to behave more like an "antenna" (RF field energy radiator).

It is therefore desirable to construct and provide a restrainer for an animal that permits animal MRI applications to be performed without suffering from the disadvantages associated with motion artifacts.

Physically, as a coil, is increased in dimensions and/or frequency, its equivalent electric circuit length increases, the coil ceases to behave like a conventional coil and begins to behave more like an RF field energy resonator or antenna. However, to take full advantage of the high SNR offered by the TEM resonator, the construction of the restrainer is needed that accommodates the TEM resonator and simultaneously minimizes motion artifacts by the awake animal. Furthermore, the restrainer has to be built such that it prevents discomfort to the animal.

SUMMARY

In one aspect, a restraining assembly for an awake animal within a magnetic resonance imaging (MRI) device is provided and includes a body restrainer having a first part and a second part that hold the body of the awake animal therebetween. A volume coil for generating an excitation RF signal is provided and is removably coupled to a holder that is securely coupled to the body retainer and an RF surface coil is also provided for receiving an RF response from the animal. The RF surface coil is carried by a component that is disposed within the volume coil. The restraining assembly also includes an adjustable hip holder that has a first section that seats against and applies a restraining force to a buttocks/hip area of the animal and a second section that is adjustably coupled to a pivoting member that is attached to the first section of the body restrainer such that the hip holder is adjustable in both a longitudinal direction along a length of the body restrainer and an up/down direction within the body restrainer between the first and second parts thereof. The pivoting member has features that permit the hip holder to be locked in a desired location so that a sufficient restraining force is applied the animal when the first and second parts are closed.

In another aspect, a arm holder assembly for use in a body restrainer of a restraining assembly for an awake animal within an MRI device is provided. The arm holder assembly includes a arm holder that receives the hands of the animal and is configured to be removably mounted to the body restrainer. The arm holder has a pair of openings formed therein for receiving the hands. The arm holder assembly is also formed in part by left and right arm pieces that are removably disposed within the pair of openings of the arm holder. Each arm piece has a body with a lip portion that seats against an upper surface of the arm holder to position the arm piece relative to the arm holder and prevent the arm piece from being entirely inserted into one opening of the arm holder. The body of each arm piece effectively reduces the diameter of the opening to aid in immobilizing the arms of the animal, while still permitting the fingers of the animal to be free so that the animal can respond to applied stimuli, etc., with finger actions. Each arm piece has a locating feature that permits it to be orientated relative to the body restrainer and also prevents twisting of the arm piece within the opening.

The restraining assembly also includes a number of other features designed to hold and restrain the animal. More specifically, the restraining assembly includes a chin holder for holding and restraining the a chin of the animal. One exemplary chin holder has a base section that is removably attached to the above mentioned arm holder which is itself attached to a part of the body restrainer. The chin holder also includes a contoured chin holder member that is integrally attached to the base section and has a curved shape to permit the animal's chin to rest therein. The restraining assembly can also include a leg holder that is adjustably attached to a sloped surface that is formed as part of the second part of the body restrainer. The restraining assembly also includes a pair of chest holders that are adjustably attached to a platform that is formed as part of the second part of the body restrainer. When the animal is put into position within the body restrainer, the chest of the animal is received between vertical walls and the chest holders, which are then adjusted so that the chest is snugly received between the vertical walls.

In one preferred set up, the above-described restraining assembly is constructed to hold and restrain a rhesus monkey, preferably a 1-15 kg rhesus monkey. Moreover, the features and general construction of the present restrainer overcomes the deficiencies of earlier system for MRI animal applications since the present restrainer restrains the animal in such a way that motion artifacts are eliminated or substantially reduced during an animal application. The present set up does not require any surgical procedures to be performed, etc. and generally, the animal is in a comfortable setting. Also, conventional restraining devices often required the animal to be trained for several months to learn how to sit still before it could even be placed into the restraining device.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 17 is a perspective view of a chin holder piece for use in the restraint system of FIG. 1;

FIG. 18 is a top plan view of the chin holder piece of FIG. 17;

FIG. 19 is a front elevational view of the chin holder piece of FIG. 17;

FIG. 23 is a perspective view of a right arm piece holder that is a mirror image of the left arm piece holder of FIG. 20;

FIG. 24 is a perspective view of base member for pivotally restraining a hip holder for use in the restraint system of FIG. 1;

FIG. 25A is a perspective view of a pivotable member for use with the base member of FIG. 24;

FIG. 28A is a view of an inner surface of a printed circuit board configured for use in the volume coil;

FIG. 28B is another view of an inner surface of a printed circuit board;

DETAILED DESCRIPTION OF PREFERRED EMBODIMENTS

Figure 1:
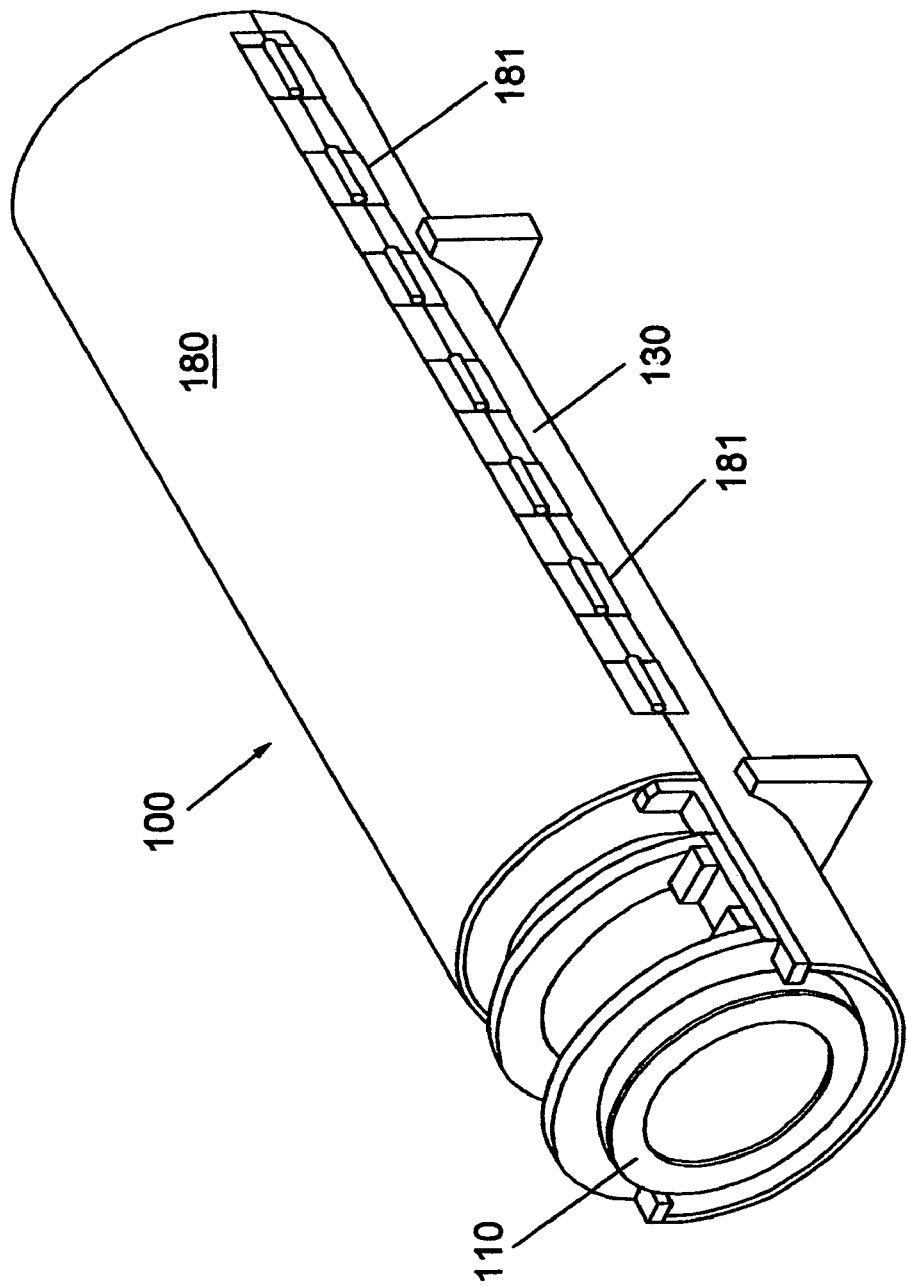
FIG. 1 is a perspective view of a dual coil restraint system (restraining assembly) in a closed position.

In the figures, like numbers are used to indicate like elements. FIG. 1 is a perspective view of a dual coil animal restrainer 100 according to a first embodiment and includes a volume coil 240 and a surface coil 300 (FIG. 33A) and it is configured to permit functional magnetic resonance imaging (fMRI) of conscious animals. FIG. 1 illustrates the restrainer 100 in the closed position. As best shown in FIGS. 1-5, the restrainer 100 is actually formed of a number of individual parts that are assembled together. More specifically, the restrainer 100 includes a holder base 130 and a cover 180 that is removably attached to the holder base 130. The holder base 130 is a shaped article that is preferably formed of a plastic material or the like; however, other types of non-magnetic materials can be used to form the holder base 130. The holder base 130 is formed of a body section 132 having a first end 134 and an opposing second end 136. The body section 132 is generally arcuate in shape and in one embodiment, the body section 132 has a generally hemi-spherical shape and is defined by an inner surface 138 and an opposing outer surface 140. The body section 132 terminates at two edges 142 that are spaced apart from one another and are orientated about 180 degrees from one another. Each of the two edges 142 includes a guide rail 144 disposed proximate the first end 134 and more specifically, the guide rail 144 extends from the first end 134 to a point 135 near the first end 134. The guide rail 144 has a first section 146 that is axially aligned with and parallel to the edge 142 and extends from the point 135 to the first end 134. The first section 146 includes a smooth, planar top surface 147 and in one exemplary embodiment, the first section 146 has a rectangular cross-section. The guide rail 144 has a second section 148 that is formed near the point 135 and is a segment of the guide rail 144 that is perpendicularly orientated relative to the first section 146. As illustrated, the second section 148 extends a short distance upward from the top surface 147 of the first section 146, thereby creating a vertical wall 150 that provides a smooth, planar surface at the point 135.

The body section 132 is intended to rest on a surface and therefore, a plurality of legs or the like 152 are provided along the outer surface 140 thereof. Because the body section 132 has an arcuate shape, the legs 152 are provided so that the body section 132 can rest on a planar surface, such as a floor. Each leg 152 is in the form of a support member that has an arcuate upper surface 154 that is shaped to receive and hold the body section 132 and therefore, in one exemplary embodiment, the upper surface 154 has an arcuate shape. The leg 152 also includes a planar lower surface 156 that seats against the support surface, such as the floor, etc. The leg 152 has a pair of side edges 157 that are perpendicular to the lower surface 156. The legs 152 provide a solid foundation for the restrainer 100 and prevent undesired movement, i.e., rolling, etc., of the body section 132. In the exemplary embodiment, the body section 132 is supported by two legs 152 that are spaced apart from one another, one near the first end 134 and the other near the second end 136.

The inner surface 138 of the body section 132 also has a number of other features. For example, the inner surface 138 is not a smooth surface but rather, the inner surface 138 includes a raised platform 160 and a sloped ramp structure 170. More specifically, the raised platform 160 is formed in an intermediate region of the body section 132 and includes a top planar surface 162 that extends from a first edge 163 to a second edge 164. Because the platform 160 is raised relative to the inner surface 138 of the body section 132, a vertical wall 165 is formed at the first edge 163. The vertical wall 165 is formed substantially perpendicular to the platform 160 at the first edge 163 thereof. Because of the arcuate shape of the inner surface 138, the vertical wall 165 is generally hemi-spherical in shape. At the second edge 164, the raised platform 160 transitions into the sloped ramp structure 170. Preferably, this is a seamless transition, since the raised platform 160 and the ramp structure 170 is a single integral piece (e.g., a single molded piece). The ramp structure 170 has one end that terminates at the second edge 164 and it slopes downward toward the inner surface 138 of the body section 132 until it joins the inner surface 138. The ramp structure 170 thus extends between the sides of the body section 132.

Many of the above components of the body section 132 contain features that permit other components of the restrainer 100 to be detachably coupled to the body section 132 or features that permit the animal to be disposed within the restrainer 100 with an extra degree of comfort. For example, the top surface 147 of the first section 146 of each of the guide rails 144 includes one or more openings 149 formed therein to receive fasteners or the like to couple another external component to the body section 132, as will be described in greater detail hereinafter. In addition, the planar platform 160 and the ramp structure 170 can have a series of openings 151 formed therein for receiving fasteners to detachably couple other parts to the body section 132 as will be described in greater detail hereinafter. For example, the planar platform 160 can include a set of openings 151 spaced apart from one another and axially arranged near one edge 142 of the body section 132 and another set of similar openings 151 are formed near the other edge 142 of the body section 132. These openings 151 can have any number of different sizes and shapes. For example, the openings 151 can be circular openings or they can be in the form of elongated slots. In addition, the ramp structure 170 can include a number of openings 151 formed therein. In the illustrated embodiment, there are a number of openings 151 that are axially aligned along the ramp structure 170. It will be appreciated that both the openings 151 on the planar platform 160 and the ramp structure 170 permit adjustment of components that are detachably coupled to the body section 132 since the openings 151 define various positions in which the components can be coupled, and thereby permit adjustment of the components. In yet another aspect, the ramp structure 170 includes a pair of knee openings or slots 169 for receiving the knees of a rhesus monkey, which is a preferred animal for use with the restrainer 100. One knee opening 169 is formed on one side of the openings 151 and the other opening 169 is formed on the other side of the openings 151.

Figure 4:
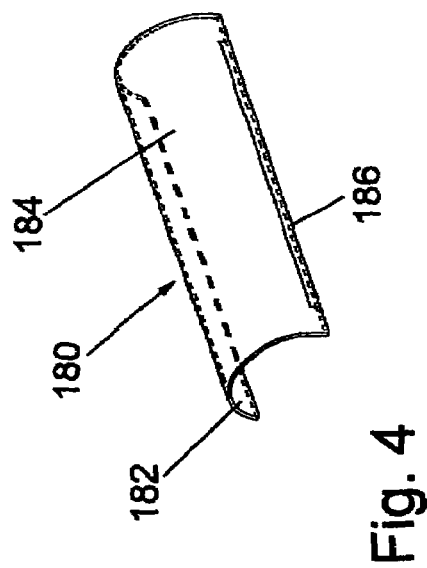
FIG. 4 is a perspective view of a cover of the restraint system of FIG. 1.

The cover 180 is constructed so that it can mate with the body section 132 to enclose a significant portion thereof. FIG. 4 is a perspective view of the cover 180. The cover 180 is generally hemi-spherically shaped and it has an inner surface 182 and an opposing outer surface 184. The cover 180 is also open at both of its ends and it has a width and length that are complementary to the body section 132. In other words, the length of the cover 180 and the body section 132 are substantially identical and the widths of the two are also substantially identical so that edges 186 of the cover 180 seat against edges 142 of the body section 132. As best shown in FIG. 1, the cover 180 is pivotally attached to the body section 132 and in one exemplary embodiment, the cover 180 is hingedly attached to the body section 132 using a plurality of hinges 181 that are disposed along the edge 142 of the body section 132. The cover 180 thus opens in a hinged manner along the edge 142.

Figure 7:
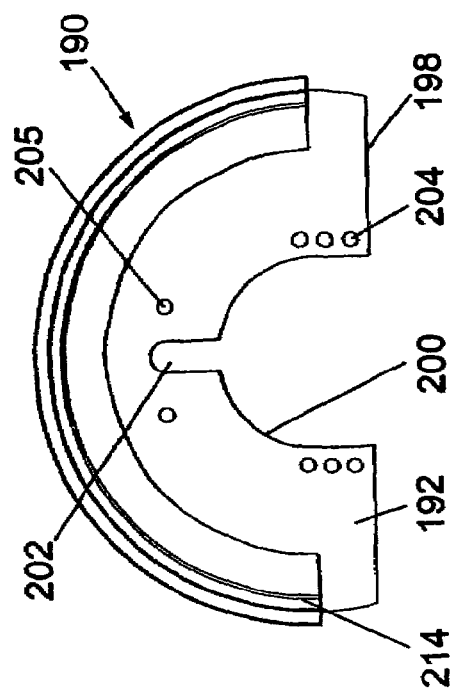
FIG. 7 is an end elevational view of the connector plate of FIG. 6.
Figure 6:
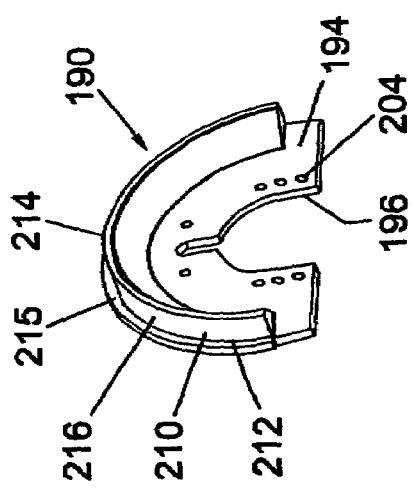
FIG. 6 is a perspective view of the connector plate for use in the restraint system of FIG. 1.

The restrainer 100 also includes a connector plate 190 that serves as a support structure and is best shown in FIGS. 6-7. The connector plate 190 is also preferably formed of a plastic material (e.g., a molded article) or a non-magnetic material as a single part. The connector plate 190 is formed of a body 192 having a first face 194 and an opposing second face 196. One exemplary body 192 has a hemi-spherical shape that is defined in part by a planar lower edge 198. The body 192 has an opening 200 formed therein and in the illustrated embodiment, the opening 200 is a U-shaped opening with a slot 202 extending therefrom at an upper section of the opening 200. The slot 202 is an elongated, oblong shaped slot. Because the opening 200 is centrally formed, it generally divides the body 192 into first and second sections (head and shoulder sections).

The body 192 also includes a number of other openings 204, 205 that are formed in the body 192 at select locations. For example, a first set of openings 204 are formed on one side of the opening 200 and a second set of openings 204 are formed on the other side of the opening 200. In the illustrated embodiment, each set of openings 204 includes a plurality of openings that are axially aligned (e.g., three openings 204). The openings 205 are formed proximate the slot 202 with one opening 205 being formed on one side of the slot 202 and the other opening 205 being formed on the other side of the slot 202. The size and shape of each of the openings 204, 205 can vary depending upon the precise application, e.g., the openings 204, 205 can have a circular shape or any other shape. The openings 204, 205 are designed to receive fasteners for mechanically attaching various components.

The connector plate 190 also includes a peripheral flange 210 that extends around a circumferential length of the body 192. In the illustrated embodiment, the peripheral flange 210 does not extend completely to the lower edge 198 of the two sections. Further, the peripheral flange 210 extends outwardly from the first face 194 and one edge 212 thereof extends beyond a peripheral edge of the body 192. The peripheral flange 210 has a triangular cross-section defined in part by the one edge 212 and another edge 214 that is an outermost edge of the peripheral flange 210. Thus, the peripheral flange 210 has a pair of sloped surfaces 216 that terminate at the edge 214 and a shoulder 215 is formed near the one edge 212. Preferably, the connector plate 190 is formed of a plastic material and is formed as a single integral part.

Figure 2:
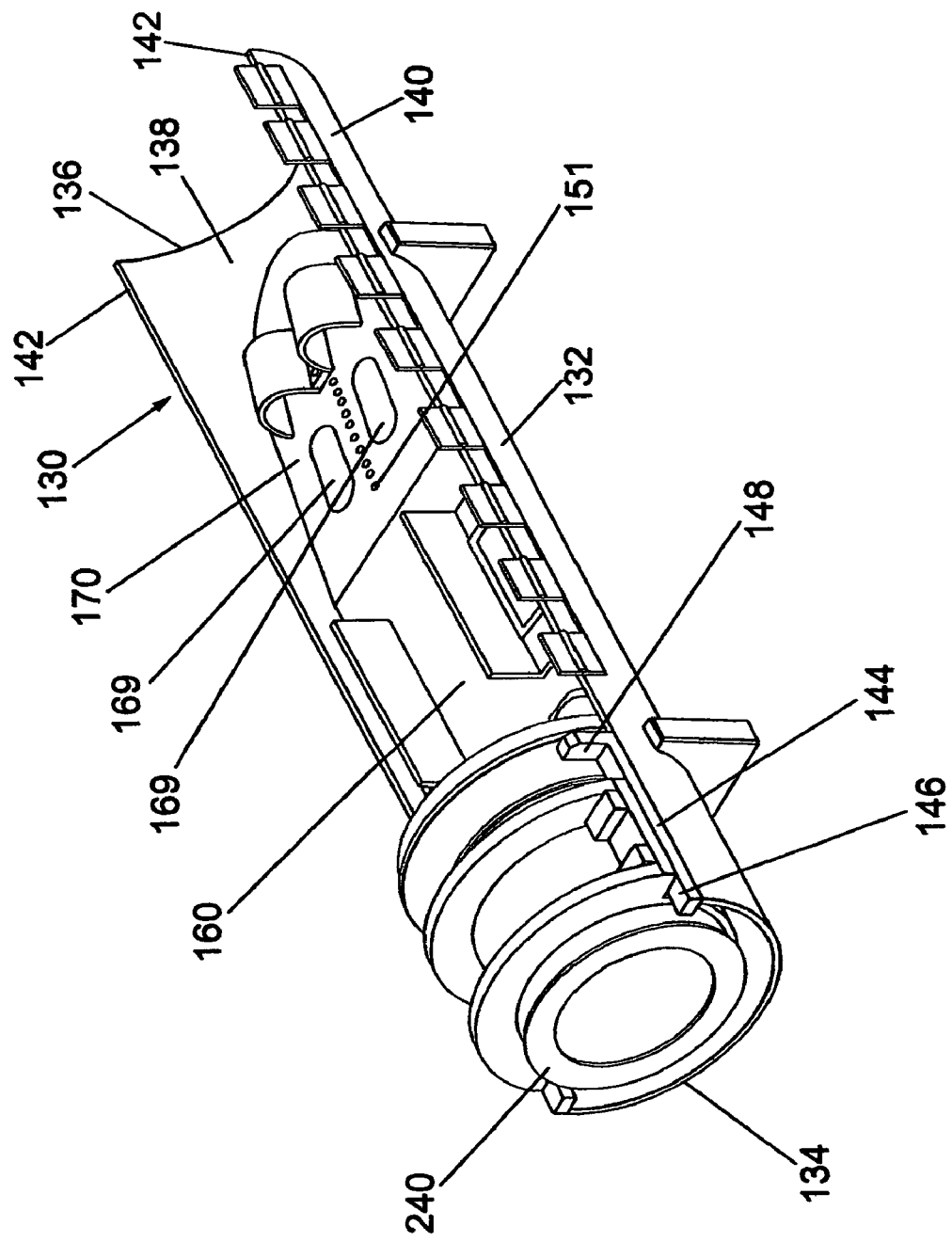
FIG. 2 is a perspective view of a lower section of the restraint system of FIG. 1.
Figure 3:
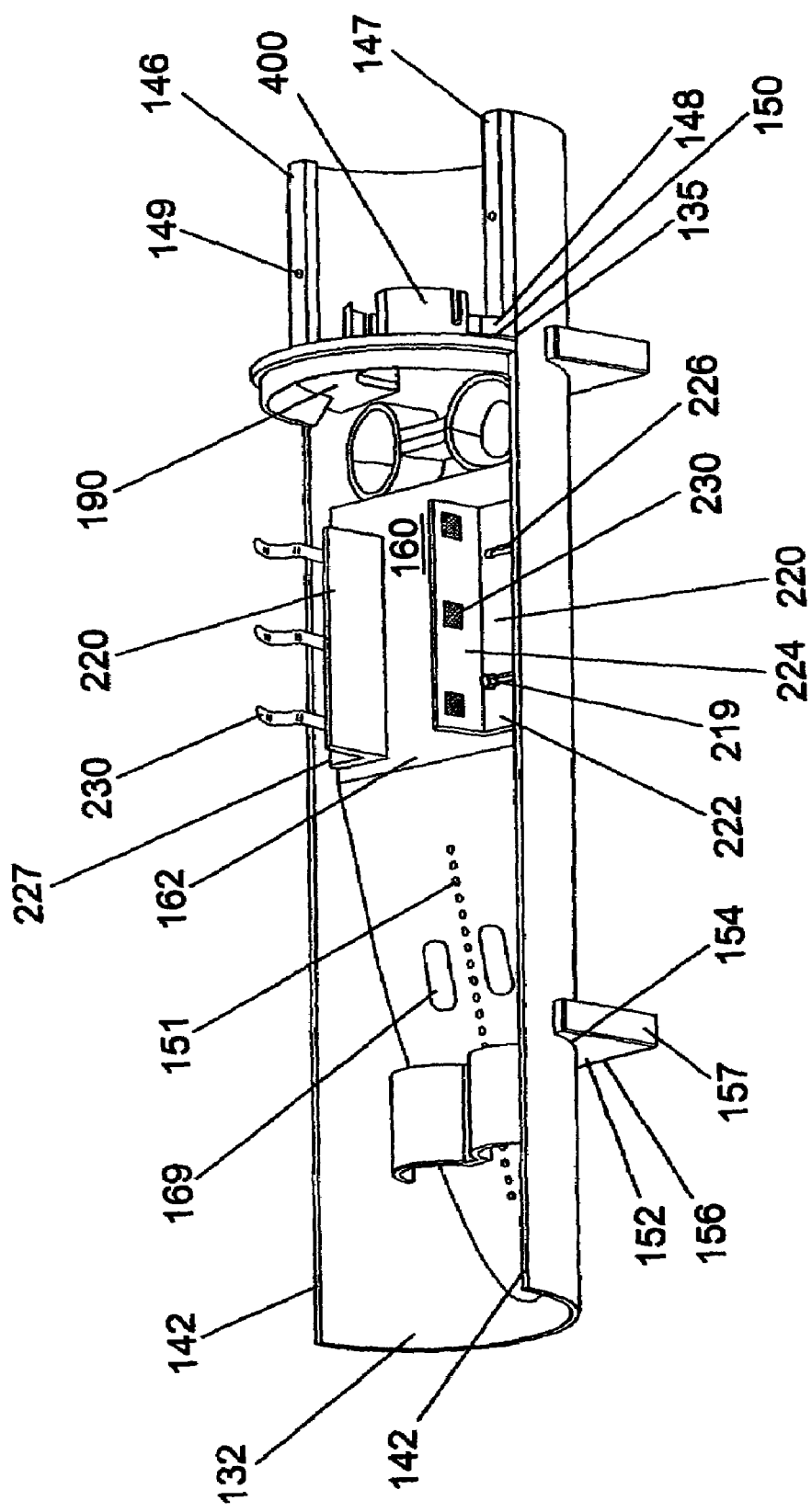
FIG. 3 is another perspective view of the lower section of the restraint system of FIG. 1.
Figure 5:
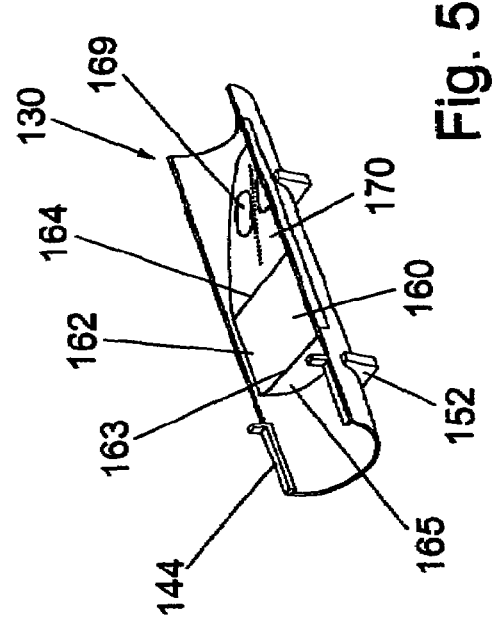
FIG. 5 is a perspective view of a holder base of the restraint system of FIG. 1.

As best shown in FIGS. 2-3 and 6, the connector plate 190 is securely attached to the body section 132 of the holder base 130 such that the peripheral flange 210 extends toward the second end 136 of the body section 132 and the second face 196 of the connector plate 190 seats against the guide rail 144 and more particularly, the connector plate 190 is placed in an abutting relationship with the second section 148 of the guide rail 144 (i.e., the vertical wall 150). The connector plate 190 thus extends across the body section 132 between the edges 142 thereof. The connector plate 190 provides a member which receives the cover 180 of the restrainer 100. More specifically, one end of the cover 180 is disposed against the connector plate 190 in an abutting relationship and more specifically, the cover 180 seats against the shoulder 215. Because the cover 180 is preferably hingedly connected to the body section 132, the cover 180 can be positioned between an open position and a closed position in which one end of the cover 180 seats against the shoulder 215.

The restrainer 100 also includes a pair of adjustable chest holders 220 that are disposed on and secured to the platform 160. Each chest holder 220 is generally in the form of a bracket that includes a first section 222 and a second section 224 that is connected to the first section 222. In one exemplary embodiment, the first and second sections 222, 224 are connected to one another at a right angle, and thus, the chest holder 220 is in the form of an L-shaped bracket. The first section 222 of the chest holder 220 is disposed flush against the platform 160, with the second section 224 being vertical to the platform 160 and extending outwardly therefrom. The chest holder 220 has a number of slots 226 formed therein for receiving fasteners 219 that securely attach the chest holder 220 to the platform 160 of the body section 132. More specifically, the first section 222 of the chest holder 220 includes the slots 226 that are open at an edge 227 of the first section 222. The slots 226 terminate at a location near the junction between the first and second sections 222, 224. In the illustrated embodiment, there are at least two slots 226 that are spaced apart from one another along the length of the edge 227 of the first section 222. The slots 226 are axially aligned with corresponding openings formed in the platform 160 so that fasteners can be received through the slots 226 and the openings so as to securely attach the chest holder 220 to the platform 160. Because the slots 226 have a length, the chest holder 220 is adjustable relative to the edge 142 of the body section 132. Because the second sections 224 face one another, an unobstructed space is formed between the second sections 224 and this space is designed to receive the torso and more specifically, the chest region of the animal (e.g., rhesus monkey). The chest holders 220 are thus adjustable so that they seat against the chest of the animal. In other words, the distance between the second sections 224 can be varied and this permits the chest holders 220 to be positioned so that they securely hold the animal therebetween. The fasteners can be any number of traditional fasteners, such as locking thumb screws, etc.

The pair of chest holders 220 can also include additional securing means that is disposed thereon or formed as part thereof to secure the animal between the chest holders 220. For example, the chest holders 220 can include hook and loop type fasteners 230 that are disposed on each of the chest holders 220. The hook component can be disposed on one of the chest holders 220 and the loop component in the form of a strap can be attached to the other of the chest holders 220. After the animal is positioned between the chest holders 220, the chest holders 220 are then adjusted so that they seat against the animal's chest. The additional securing means, such as the hook and loop type fasteners 230, are then adjusted so that the animal is securely held between the chest holders 220.

As previously mentioned, the restrainer includes a volume coil 240 and it has a volume coil holder 340 (FIG. 8) for holding the volume coil 240 in a preselected location. The volume coil 240 is preferably of the type that is disclosed in U.S. patent application Ser. No. 09/694,087, which has previously been hereby incorporated by reference in its entirety. Both the volume coil 240 and the surface coil 300 (FIG. 33A) are connected via wiring which extends to a transceiver unit 312 of a system operating controller 320 as explained in greater detail hereinafter. In one embodiment, the volume coil 240 transmits and the surface coil 300 is used for receiving. In other embodiments, the surface coil 300 both transmits and receives or the volume coil 240 both transmits and receives.

Figure 8:
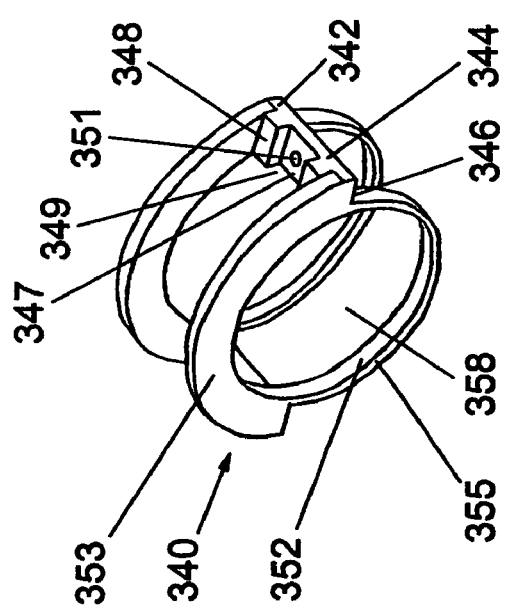
FIG. 8 is a perspective view of a coil holder for use in the restraint system of FIG. 1.
Figure 10:
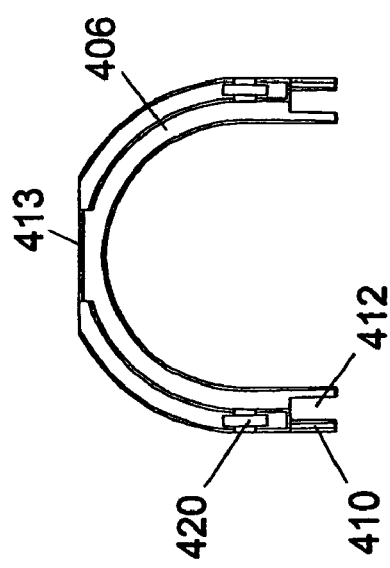
FIG. 10 is an end elevational view of the head holder of FIG. 9.

The volume coil holder 340 for holding the volume coil 240 is best shown in FIG. 8. The coil holder 340 has a pair of opposing base sections 342 that are constructed to be disposed on the first section 246 of the guide rail 244. More specifically, each base section 342 includes a longitudinal beam 344 that has a lower planar surface 346 that seats on the first sections 246 of the guide rails 244. The base section 342 also includes two blocks 348 that are preferably integrally formed as part of the longitudinal beam 344 and extend upwardly from an upper planar surface 347 thereof. A space 349 is formed between the two blocks 348 with an opening 351 being formed through the longitudinal beam 344 within the space 349. When the volume coil holder 340 is disposed on the first sections 246 of the opposing guide rails 244, opening 351 aligns with the opening 149 formed in the first section 246 and fasteners or the like are disposed through the openings 351, 149, thereby securely attaching the volume coil holder 340 to the body section 132.

The volume coil holder 340 has two ring-like structures 352 formed at each end of the longitudinal beam 344. Each ring-like structure 352 is integrally attached to one end of the opposing base sections 342. In other words, the two base section 342 are spaced apart from one another and are arranged in a parallel relationship. The ring-like structures 352 are formed perpendicular to the base sections 342, with the base section 342 dividing the ring-like structure 352 into an upper half 353 and a lower half 355. The upper half 353 has a greater width (radius) compared to the lower half 355 since the upper half 353 of each ring-like structure 352 extends across the entire width of the base section 342 to increase the robustness of the integral attachment between the ring-like structures 352 and the base sections 342.

The ring-like structures 352 define a circular opening 358 through which the volume coil 240 can be disposed and held in a secure manner. The opening 358 thus has a diameter that is slightly greater than an outer diameter of the volume coil 240 so that the volume coil 240 is securely held in place by the ring-like structures 352. The volume coil 240 extends completely through both of the ring-like structures 352. Accordingly, the volume coil holder 340 is detachably attached to the body section 132 near or at the first end 134 thereof. As with the other components, the volume coil holder 340 can be formed of any number of materials, such as a plastic material (e.g., as an integral plastic member) or a non-magnetic material.

Figure 9:
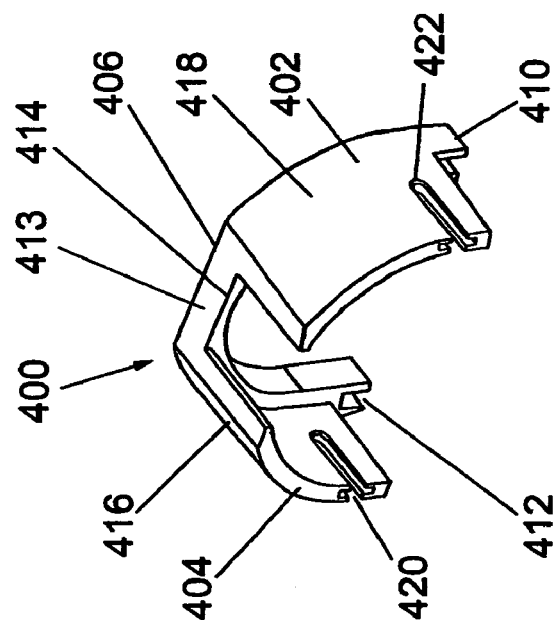
FIG. 9 is a perspective view of a head holder that is used in the restraint system of FIG. 1.

The restrainer 100 also includes a head holder 400 that is detachably attached to connector plate 190. FIG. 9 best illustrates the head holder 400 which includes a body 402 that has a front section 404 and an opposing rear section 406. The rear section 406 of the head holder 400 is detachably attached to the second face 196 of the connector plate 190 using the first and second sets of openings 204 that are formed on either side of the opening 200. The body 402 has a pair of flange members or legs 410 that extend downwardly from a lower section of the body 402. Each leg 410 has a slot 412 formed therein for receiving one or more fasteners (not shown) that extend through the slot 412 and into corresponding openings 204 formed in the connector plate 190. For example, the openings 204 can be threaded openings that receive the fasteners in a threading manner.

The head holder 400 has a planar section 413 (e.g., a flat) that is an uppermost section thereof. The planar section 413 has an opening or cutout section 414 formed therein and in one exemplary embodiment, the opening 414 has a rectangular shape. The opening 414 is open at the front section 404 and extends toward but not completely to the rear section 406. The head holder 400 also includes first and second arcuate sections 416, 418 that are each formed between one leg 410 and one edge of the planar section 413. Each of the first and second arcuate sections 416, 418 has a slot 420 formed therein. The slot 420 is open at the front section 404 and extends toward the rear section 406. One exemplary slot 420 is U-shaped with the closed end 422 of the slot 420 being near the formation of the leg 410.

The head holder 400 is attached to the second face 196 of the connector plate 190 by positioning the rear section 406 against the second face 196 so that the slots 412 of the legs 410 align with the openings 204 and fasteners, e.g., screws, are disposed through the slots 412 and into corresponding openings 204. The front section 404 thus extends away from the connector plate 190. As best shown in FIGS. 2-3, when the head holder 400 is attached to the connector plate 190, the head holder 400 is disposed above the inner surface 138 of the body section 132. The head holder 400 is constructed for receiving a head of the animal (e.g., rhesus monkey) that is contained and held within the restrainer 100.

Figure 11:
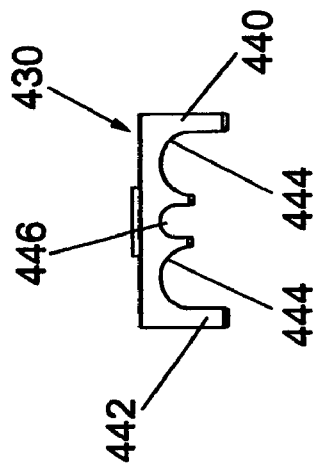
FIG. 11 is an end elevational view of a hip holder for use in the restraint system of FIG. 1.
Figure 13:
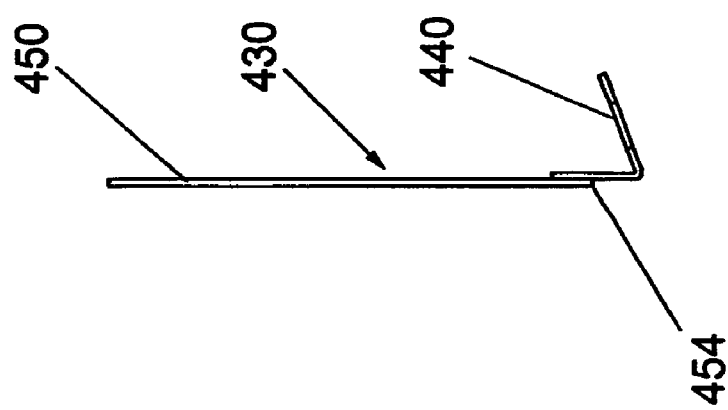
FIG. 13 is a side elevational view of the hip holder of FIG. 11.
Figure 12:
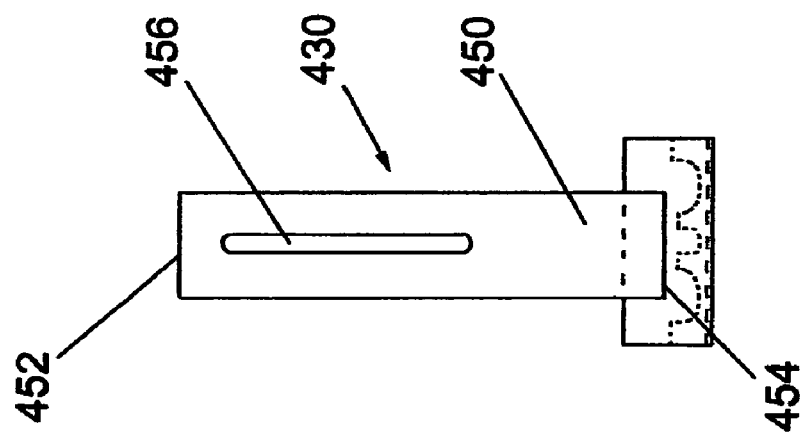
FIG. 12 is a top plan view of the hip holder of FIG. 11.

Now referring to FIGS. 11-13 in which one exemplary hip holder 430 is illustrated. In use, the hip holder 430 is disposed over the ramp structure 170 and its precise position relative thereto varies depending upon the precise application (e.g., the size and body shape of the animal). The illustrated hip holder 430 is formed of two parts, namely a main hip section 440 and an elongated section 450 that extends from the main hip section 440. The main hip section 440 is integrally connected to the elongated section 450 at a preselected angle which is less than 90 degrees (e.g., 70 degrees). The main hip section 440 is contoured to fit around the hip region of the animal that is received and held within the restrainer 100. For example, the main hip section 440 includes a pair of side leg sections 442 that are defined partially by a pair of arcuate surfaces 444 that extend inwardly from the pair of leg sections 442. The arcuate surfaces 444 are designed to seat against the buttocks area of the monkey when the monkey is held within the restrainer 100 in the proper position as described in greater detail hereinafter. In one exemplary embodiment, each arcuate surface 444 has a semi-circular shape. The main hip section 440 also includes a slot or opening 446 for receiving the tail of the monkey when the hip holder 430 is disposed against the hip/buttocks areas of the monkey. In the illustrated embodiment, the opening 446 is a U-shaped slot that is formed between the pair of arcuate surfaces 444. The U-shaped slot 446 is thus centrally located.

The elongated section 450 is an elongated planar member that has a first end 452 that is pivotally attached to and locked in place relative to the body section 132 and it has an opposing second end 454 where the main hip section 440 is integrally attached thereto. The elongated section 450 has a closed ended slot 456 that is formed therein. The slot 456 is formed such that a longitudinal axis thereof is parallel to side edges 451 of the elongated section 450. In the illustrated embodiment, the slot 456 has a length that is greater than 50% of the length of the elongated section 450 itself.

The hip holder 430 is designed to be locked into a predetermined position relative to the body section 132 and more specifically, relative to the cover 180. The means for accomplishing the aforementioned includes a base member 460 that is shown in FIG. 24 and a pivotable member 470 that is best shown in FIG. 25. The base member 460 includes a pair of legs 462 that are spaced apart from one another and are integrally attached at one end to a wall 464 that extends thereacross. A gap 463 is thus formed between the pair of legs 462. The wall 464 has a flange-like member 465 that is formed at one end of the wall 464 and extends outwardly therefrom beyond the legs 462. More specifically, the flange-like member 465 is crescent shaped and has pointed ends 467 that extend beyond the legs 462. An upper surface 469 of the flange-like member 465 is a curved surface that is complementary to the inner surface of the cover 180 so that the flange-like member 465 can seat against and be attached to the inner surface of the cover 180 at a prescribed location. For example, the upper surface 469 can be welded (e.g., sonically) to the inner surface of the cover 180 with the legs 462 extending downwardly therefrom.

Each leg 462 has a number of openings 461 formed therein. For example, each leg 462 according to one embodiment includes a pair of openings 461 formed therein. The openings 461 in one leg 462 are preferably axially aligned with the openings 461 that are formed in the other leg 462. While FIG. 24 illustrates the openings 461 as being circular shaped openings, it will be appreciated that the openings 461 can have any number of different shapes.

Figure 25B:
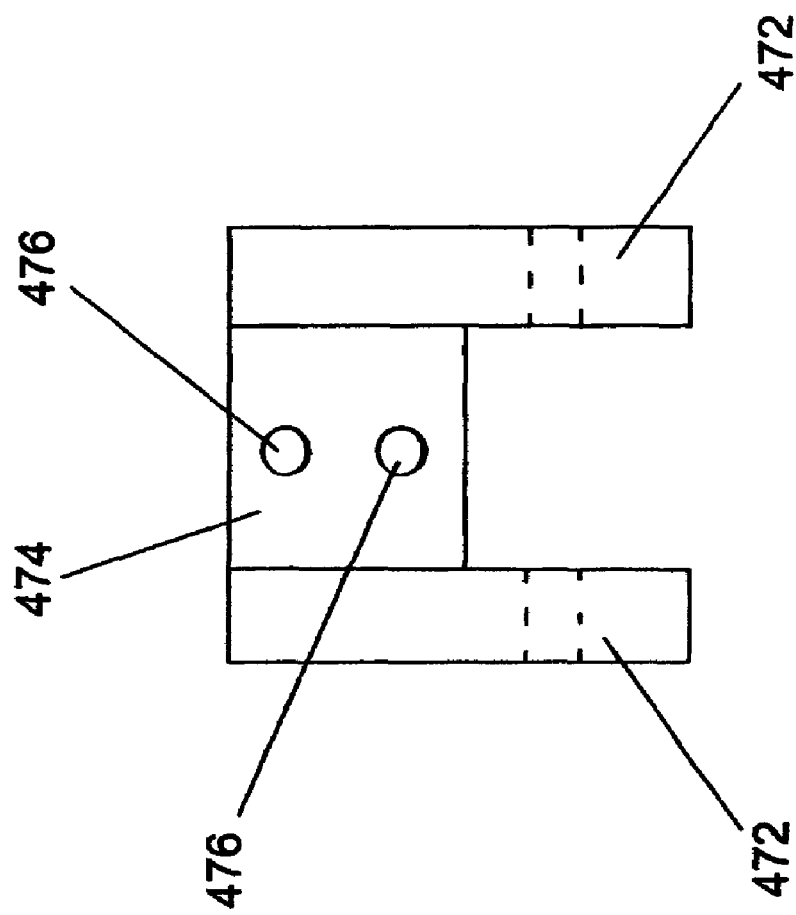
FIG. 25B is a top plan view of the pivotable member of FIG. 25A.

As shown in FIGS. 25A and 25B, the pivotable member 470 is a separate member from the base member 460 and is configured so that the pivotable member 470 can be pivotally connected to the base member 460. The pivotable member 470 includes a pair of spaced vertical walls 472 and a base wall 474 that is integrally attached to first ends of the vertical walls 472 and extends across the gap formed between the vertical walls 472. In other words, the vertical walls 472 are integrally connected to the base wall 474 at its two ends. In one exemplary embodiment, the base wall 474 is rectangular shaped and it includes at least one opening or slot 476 formed therethrough. For example, the base wall 474 can include two openings 476 that are circular shaped and extend completely through the base wall 474.

Each vertical wall 472 includes a number of openings or slots formed therein and according to one exemplary embodiment, each vertical wall 472 has an opening 478 and a slot 480 formed completely therethrough. The openings 478 (e.g., circular shaped openings) are axially aligned with one another and the slots 480 are likewise axially aligned with one another. At one end, each vertical wall 472 has a curved portion 482 that extends beyond the edge of the base wall 474. Preferably, the curved portion 482 extends from the bottom edge to the top edge of the vertical wall 472. In other words, it extends the complete height of the vertical wall 472. Preferably, the openings 478 are formed in the curved portions 482 since these openings 478 receive a pin or the like to permit the pivotable member 470 to pivot relative to the base member 460 as discussed in greater detail below.

The pivotable member 470 is received between the legs 462 of the base member 460 which is securely attached to the inner surface of the cover 180. In placing the pivotable member 470 between the legs 462, it is arranged so that the openings 478 are closest to the end 136 of the body section 132 and the base wall 474 is spaced from the wall 464 (with both the legs 462 and vertical walls 472 being disposed between the walls 464 and 474). The openings 478 are aligned with one pair of openings 461 and a pivot pin or the like (e.g., a hinge pin) is received therethrough to define a pivot axis of the pivotable member 470. At the same time, locking fasteners (not shown) are received through the other openings 461 and into the slots 480 so as to effectively lock the pivotable member 470 relative to the base member 460. More specifically, the pivotable member 470 is freely pivotable about the pivot pin until the user finds a desired location for the pivotable member 470 (i.e., a desired angle between the pivotable member 470 and the base member 460 is determined) and then the user locks the pivotable member 470 in place by inserting one or more locking fasteners through the openings 461 into the slots 480 to effectively prevent any further pivoting of the pivotable member 470 relative to the base member 460. One exemplary type of locking fasteners is a locking thumb screw.

The elongated section 450 of the hip holder 430 is adjustable and lockingly attached to the pivotable member 470 so that the elongated section 450 can be maintained in a desired position when the cover 180 is shut relative to the body section 132. The hip holder 430 is intended to apply pressure to the buttocks and hips of the animal so that the animal is effectively held in place within the body section 132 and its movements therein are restricted. The hip holder 430 thus especially restricts the up and down movements of the animal. The elongated section 450 is locked in place relative to the pivotable member 470 by placing the elongated section 450 underneath the base wall 474 such that the slot 456 formed in the elongated section 450 is axially aligned with at least one of the openings 476 formed in the wall 474. The hip holder 430 is then moved along the longitudinal axis of the body section 132 until the main hip section 440 is orientated in a desired location such that when the cover 180 is closed, the main hip section 440 will seat against the buttocks and hips of the animal. Once the optimum location of the hip holder 430 is determined, the elongated section 450 is locked in place relative to the pivotable member 470 by inserting a locking fastener (e.g., a locking thumb screw) through the slot 456 formed in the elongated section 450 and into one of the openings 476 of the wall 474. This effectively locks the elongated section 450 relative to the pivotable member 470 and prevents longitudinal movement thereof. The up and down movement of the hip holder 430 is controlled, as previously mentioned, by inserting locking fasteners through the openings 461 into the slots 480. By locking the pivotable member 470 into place, the up and down movement of the hip holder 430 is restricted and therefore, when the cover 180 is shut relative to the body section 132, the main hip section 440 seats against and applies pressure against the buttocks and hips of the animal. This area of the animal is thus effectively held and restrained in place between the hip holder 430 and the ramp structure 170.

The hip holder 430 can easily be adjusted by simply unlocking the elongated section 450 from the pivotable member 470 and then repositioning the hip holder 430 by adjusting the up/down position of the hip holder and/or the longitudinal position of the hip holder 430 within the body section 132.

Figure 14:
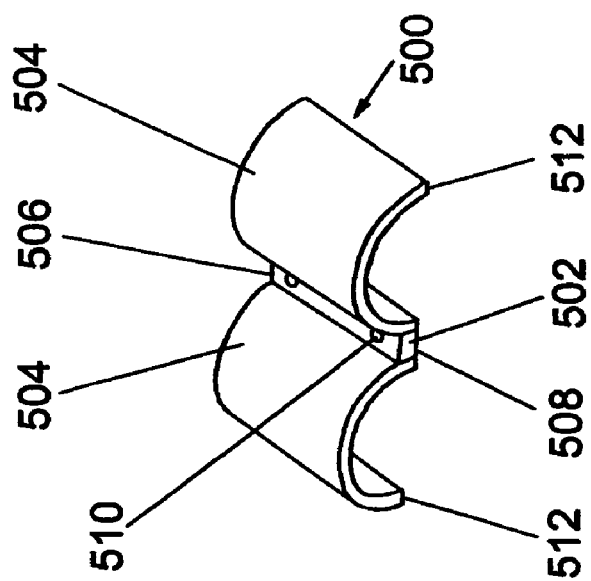
FIG. 14 is a perspective view of a leg holder for use in the restraint system of FIG. 1.

The restrainer 100 also includes a leg holder 500 that is adjustably attached to the body section 132, and more particularly, the ramp structure 170 thereof. As best shown in FIGS. 3 and 14, the leg holder 500 is preferably a single integral member that has a central base section 502 that is intermediate to a pair of opposing arcuate side sections 504. The central base section 502 has a planar upper surface 506 and a planar lower surface 508 that seats against the ramp structure 170. The base section 502 has a rectangular shape and includes one or more and preferably two or more openings 510 formed therein. At each side of the base section 502, the arcuate side sections 504 join the base section 502.

Each of the illustrated arcuate side sections 504 has a semi-circular shape to accommodate a leg of the monkey when the monkey is strapped into and held within the restrainer 100. The side bottom edges 512 of the arcuate side sections 504 lie within or lie slightly above the plane that contains the lower surface 508 of the base section 502 to permit the planar lower surface 508 to seat against the ramp structure 170. The base section 502 is disposed on the ramp structure 170 so that the openings 510 of the base section 502 are axially aligned with the openings 151 formed in the ramp structure 170. Fasteners are received through the openings 510, 151 to thereby securely couple the leg holder 500 to the body section 132. Because there are preferably two or more openings 510 formed in the base section 502 and there are a number of openings 151 formed in the ramp structure 170, the leg holder 500 can be adjusted and locked in place in a number of different locations relative to the ramp structure 170. In other words, the leg holder 500 can be moved longitudinally along the ramp structure 170 until it is in a desired location and then fasteners are threadingly disposed through the openings 510, 151 to securely attach the leg holder 500 to the ramp structure 170. The legs of the monkey are therefore received between the leg holder 500 and the ramp structure 170 and within the arcuate side sections 504 thereof and then the leg holder 500 is secured in place against the ramp structure 170.

It will be appreciated that the precise arcuate nature of the side sections 504 can be varied to accommodate different sized legs of different animals. For example, one monkey may have larger legs than another and therefore, the degree of curvature of the arcuate side sections 504 is greater than in the case where the monkey has smaller legs. The leg holder 500 is also positioned in view of the locations of the knee openings 169 so that the monkey is comfortably orientated in the restrainer 100 with the knees extending through the knee openings 169 and the legs being secured by the leg holder 500.

Figure 16:
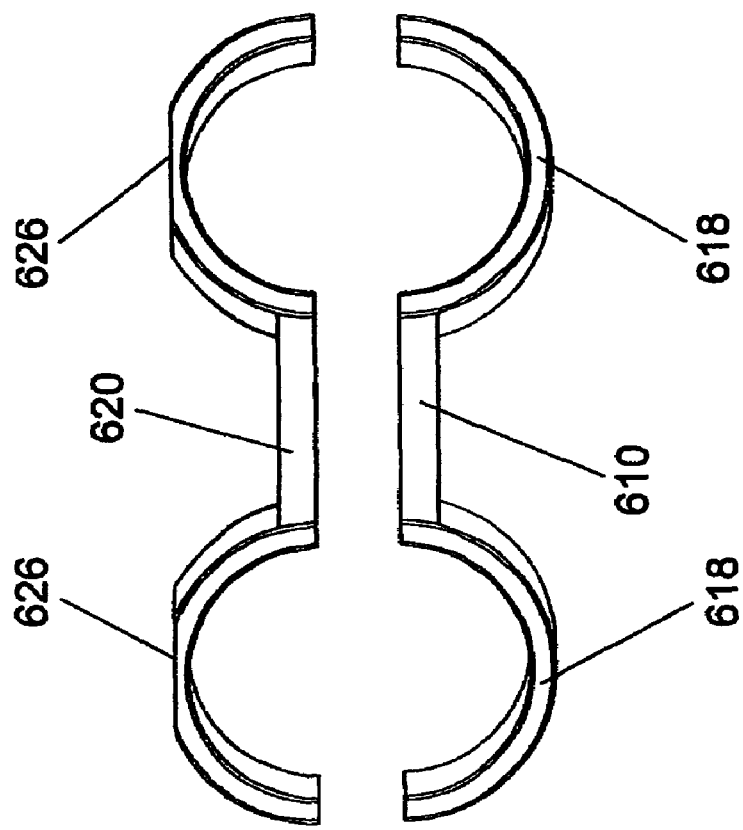
FIG. 16 is an exploded top plan view of the front and rear arm holder bases of FIG. 15.
Figure 15:
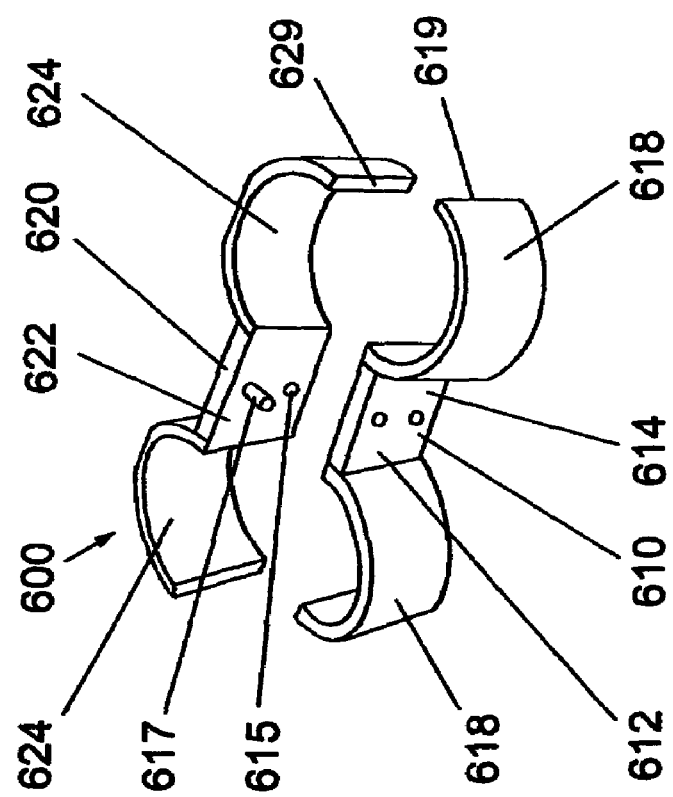
FIG. 15 is an exploded perspective view of front and rear arm holder bases for use in the restraint system of FIG. 1.

Referring now to FIGS. 15-16, the restrainer 100 also includes a arm holder 600 formed of first and second arm holder members 610, 620 that are designed to be disposed around the wrist regions of the animal so as to hold the hands of the animal in place and prevent excessive movement of the arms and hands of the animal. The first and second arm holder members 610, 620 are similar in construction but not identical and are designed to mate together to capture the arms (i.e., wrist) of the animal. Similar to the leg holder 500, the first arm holder member 610 has a central base section 612 that has first and second opposing faces 614, 616. At each end of the central base section 612, an arcuate side section 618 is formed such that the base section 612 is disposed between the arcuate side sections 618. The arcuate side sections 618 extend outwardly from the ends of the base section 612 and terminate in edges 619 that either lie within the plane of the second face 616 or slightly above this plane. In one exemplary embodiment, the arcuate side sections 618 have semi-circular shapes.

The second holder member 620 is similar to the first holder member 610 in that it includes a central base section 622 and a pair of arcuate side sections 624 that extend outwardly from the central base section 622 and terminate in edges 629. The arcuate side sections 624 are different from the arcuate side sections 618 in that each of the arcuate side sections 624 includes a planar section or flat 626 formed as part thereof. The flats 626 are formed in the same positions on the arcuate side sections 624 so that the second holder member 620 can seat against a planar surface of another component to facilitate coupling the arm holder 600 thereto. For example, the second arm holder 620 is attached to the body section 132 by positioning the flats 626 against the vertical wall 165 of the platform 160 and then attaching it thereto using conventional means, such as the use of fasteners or the use of an adhesive material.

Each of the first and second arm holders 610, 620 includes at least one threaded opening 615 formed in the base sections 602, 622, respectively. While one threaded opening 615 is shown in FIG. 15, it will be appreciated that additional threaded openings 615 can be formed in the base sections 602, 622. These threaded openings 615 can be used to receive a fastener or the like which serves to couple the first and second arm holders 610, 620 together. The second arm holder 620 can include a locating post or nub 617 that extends outwardly from an inner surface of the base section 622. The locating post or nub 617 mates with a complementary opening 619 formed in the first arm holder 610 to facilitate the alignment and coupling of the first and second arm holders 610, 620. Once the second arm holder 620 is securely attached to the vertical wall 165 of the platform 160, the first arm holder 610 can be positioned near the second arm holder 620 and the monkey's arms can be disposed between the first and second arm holders 610, 620. The first and second holders 610, 620 are then securely attached to one another with the monkey's arms disposed therebetween. When the first and second holders 610, 620 are mated together, the first surfaces of the base sections 602, 622 seat flush against one another and the edges 609 align and seat against one another.

Referring now to FIGS. 17-19, a chin holder 700 is provided for receiving and holding the chin area of a monkey that is held within the restrainer 100. The chin holder 700 includes a connector arm 702 that detachably attaches the chin holder 700 to the arm holder 600. The connector arm 702 includes a longitudinal section 704 that has a first end 706 and a second end 708. At the first end 706, a first vertical section 710 extends downwardly from the longitudinal section 704 and similarly, a second vertical section 712 extends upwardly from the longitudinal section 704 at the second end 708. The first and second vertical sections 710, 712 thus are in the form of legs that extend outwardly from the longitudinal section 704. The lengths of each of the first and second vertical sections 710, 712 is less than the length of the longitudinal section 704 and in one exemplary embodiment, the sum of the lengths of the first and second vertical sections 710, 712 is less than the length of the longitudinal section 704.

Each of the first and second vertical sections 710, 712 includes at least one opening formed therethrough. More specifically, the first vertical section 710 includes an opening or bore 716 formed therethrough and the second vertical section 712 includes an opening or bore 718 formed therethrough. According to one exemplary embodiment, the bore 716 receives the locating post 617 of the arm holder 600 so as to locate and properly position the chin holder 700 relative to the arm holder 600.

The chin holder 700 also includes a contoured chin holder part 720 that is integrally connected with the connector arm 702 and more specifically, with an upper portion of the second vertical section 712. The chin holder part 720 is a generally U-shaped member that is open at both the first end 722 and second end 724 thereof. The chin holder part 720 is defined by an arcuate wall 726 and further, the chin holder part 720 has a number of different sections that have different slopes relative to one another. A forward section 728 of the chin holder part 720 is lower than the rear section 730 of the chin holder 720. In other words, the forward section 728 slopes down from the rear section 730. As best shown in FIGS. 17 and 19, the forward section 728 also has a slightly tapered construction in that it slightly tapers inwardly toward its end away from the rear section 730. The rear section 730 is also contoured in that the arcuate wall 726 at the end of this section furthest away from the forward section 728 is cut-away such that vertical wall sections 732 are formed. By reducing portions of the arcuate wall 726 in the rear section 730, the chin of the animal can be inserted into the holder 700 more easily since the arcuate wall 726 is not as restrictive at this end that initially receives the chin of the animal.

To attach the chin holder 700 to the arm holder 600, the locating post 617 is received through the opening 716 of the first vertical section 710 and at the same time, a fastener or the like is received through the opening 718 of the second vertical section and through the threaded openings 615 of the first and second arm holders 610, 620. This fastener thus not only couples the chin holder 700 to the arm holder 600 but it also securely attaches the first and second arm holders 610, 620 to one another.

Figure 22:
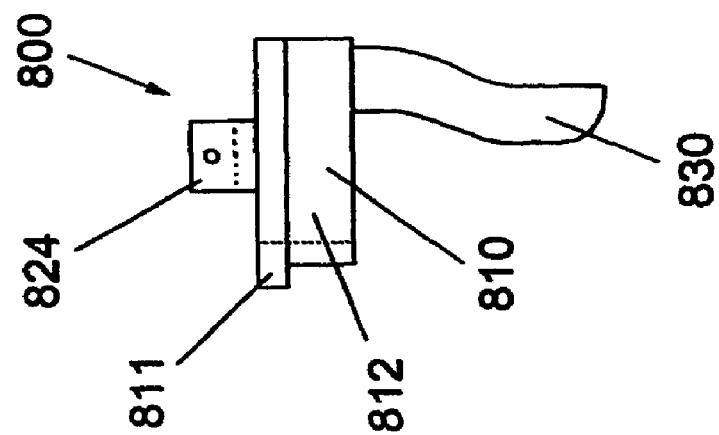
FIG. 22 is side elevational view of the left arm piece holder of FIG. 20.
Figure 21:
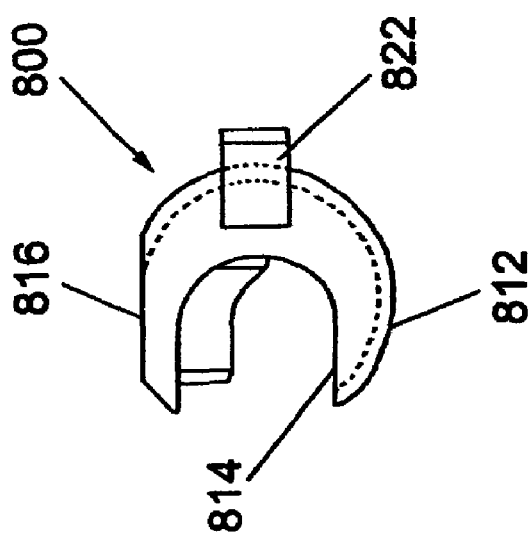
FIG. 21 is a top plan view of the left arm piece holder of FIG. 20.
Figure 20:
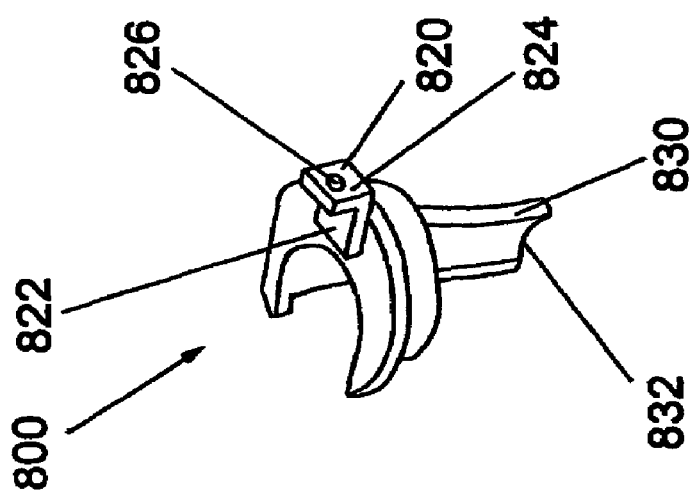
FIG. 20 is a perspective view of a left arm piece holder for use in the restraint system of FIG. 1.

Referring to FIGS. 20-22, the restrainer 100 also includes a left arm piece 800 that is removably disposed within the left cavity or opening of the arm holder 600 and a right arm piece 900 (FIG. 23) that is removably disposed within the right cavity or opening of the arm holder 600. The left arm piece 800 has a base portion 810 that is generally C-shaped and includes an outer surface 812 and an inner surface 814 that receives an upper arm region of the monkey. The inner surface 814 is a curved surface and the outer surface 812 is also a curved surface with the exception that a flat 816 is provided in one section of the outer surface 812. The formation of the flat 816 permits the left arm piece 800 to seat against the vertical wall 165 of the body section 132. The base portion 810 is actually formed of two sections, namely a first section 811 and a second section 813 that is formed below the first section 811. According to one exemplary embodiment, the first section 811 protrudes beyond the second section 813 across the entire lengths of the first and second sections 811, 813 so that it resembles a flange-like member.

The left arm piece 800 also includes a locking tab 820 that is integrally formed with the first section 811 of the base portion 810 and extends outwardly therefrom. More specifically, the locking tab 820 has a first section 822 and a second section 824 that is perpendicular to the first section 822. The second section 824 extends upwardly from the base portion 810 and preferably includes an opening 826 formed therein. Integrally formed with the second section 813 of the base portion 810 is an elongated tongue 830 that has a first end 832 that is integral with the second section 813 of the base portion 810 and an opposing second end 834 that is disposed below the second section 813. The elongated tongue 830 is arranged so that it is vertically orientated relative to the base portion 810 and therefore through the opening defined by the first and second arm holders 610, 620 and beyond the bottom faces of the first and second arm holders 610, 620. The elongated tongue 830 has a curved surface that is complementary to the curved nature of the base portion 810 and also is complementary to the general shape of the monkey's arm. More specifically, the tricep portion of the monkey's arm seats against the elongated tongue 830 when the arms are in their proper positions through the arm holder 600. The left arm piece 800 also serves to further immobilize the monkey's arms since it reduces the size of the opening in the arm holder that receives the monkey's hand and then the arm portion. In other words, it restricts the possible movement of the upper portion of the monkey's arm, while allowing the hands of the monkey to be free. As will be described hereinafter, the hands of the monkey should be free so that the monkey can give instructions to the tester as by pressing a button or the like in response to an applied stimulus or the like.

The left arm piece 800 is locked in place by positioning it such that the flat 816 seats against the inner surface 138 of the body section 132 and at the same time, the second section 824 seats against the vertical wall 165 of the body section 132 with the opening 826 formed therethrough being aligned with an opening formed in the vertical wall 165 so that a fastener can be received through respective openings so as to securely attach the left arm piece 800 to the vertical wall 165.

FIG. 23 illustrates a right arm piece 900 that is essentially identical to the left arm piece 800 with the exception that the right arm piece 900 is configured to be disposed against the opposite side of the body section 132. Accordingly, like elements are numbered alike for the left and right arm pieces 800, 900. In other words, the right arm piece 900 has a flat 816 that seats against the inner surface 138 of the body section 132 and at the same time, the second section 824 seats against the vertical wall 165 of the body section 132 with the opening 826 being aligned with an opening formed in the vertical wall 165 so that a fastener can be received therethrough to securely attach the right arm piece 900 to the body section 132.

The image processing of the present system can be performed off-line on a standard computer system, such as a Sun workstation, a 100 MHZ HP Apollo 735 workstation using IDL imaging software, Version 4.0 and higher and analyzed on a Power Mac 60/66 using NIH imaging software, Version 1.56 and higher (Apple Computer, Inc., Cupertino, Calif.). The stimulated and baseline images were subtracted to reveal regions of activation. The region of greatest activation was determined from the subtraction image. The corresponding region of the baseline and stimulated data sets were demarcated and the relative signal intensity was calculated on a pixel by pixel basis.

Figure 26:
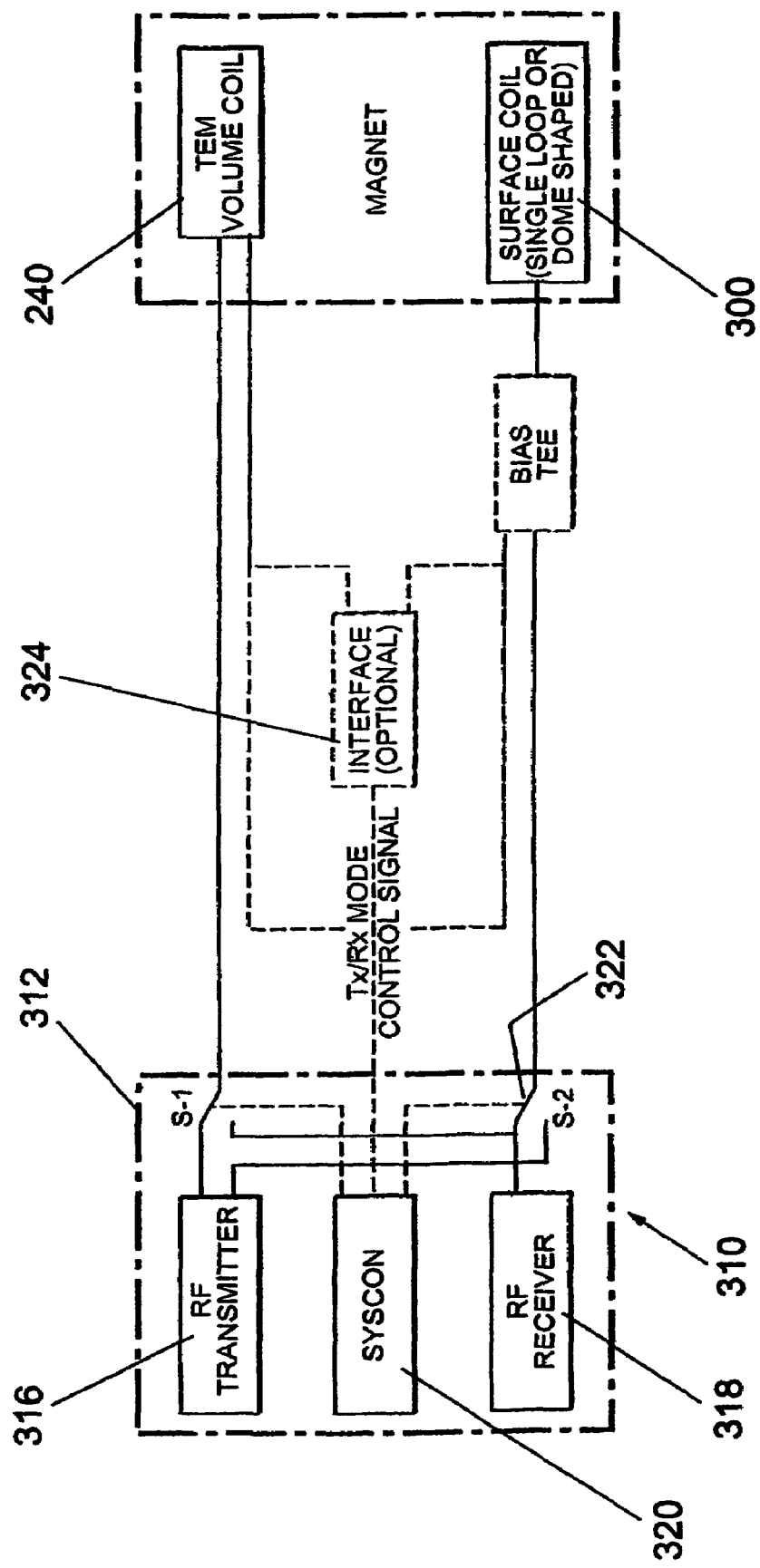
FIG. 26 is a schematic of one exemplary interface between RF-coils and an MRI transmit/receive system.

Referring to FIG. 26, a schematic of one exemplary interface between the RF coils 240 and 300 and a MRI transmit/receive system 310 is illustrated. Both the TEM volume coil 240 and the surface coil 300 are connected to the transceiver unit 312. The transceiver unit 312 has an RF transmitter 316, a single or multiple RF receiver 318 and the system controller 320. The system controller 320 controls a pair of switching circuits 322 to transmit and receive the signal from the proper coil 240 or 300. In addition, the system controller 320 also can control an interface 324 to provide active tuning/detuning of the coils. For instance, if the TEM volume coil 240, also referred to as the body coil, is active, transmitting RF energy to the animal, and the surface coil 300 (single or multiple surface coil) is detuned in order to avoid interference. Conversely, when the surface coil 300 is receiving the MR signal from the animal, the TEM volume coil 240 is detuned.

Figure 27A:
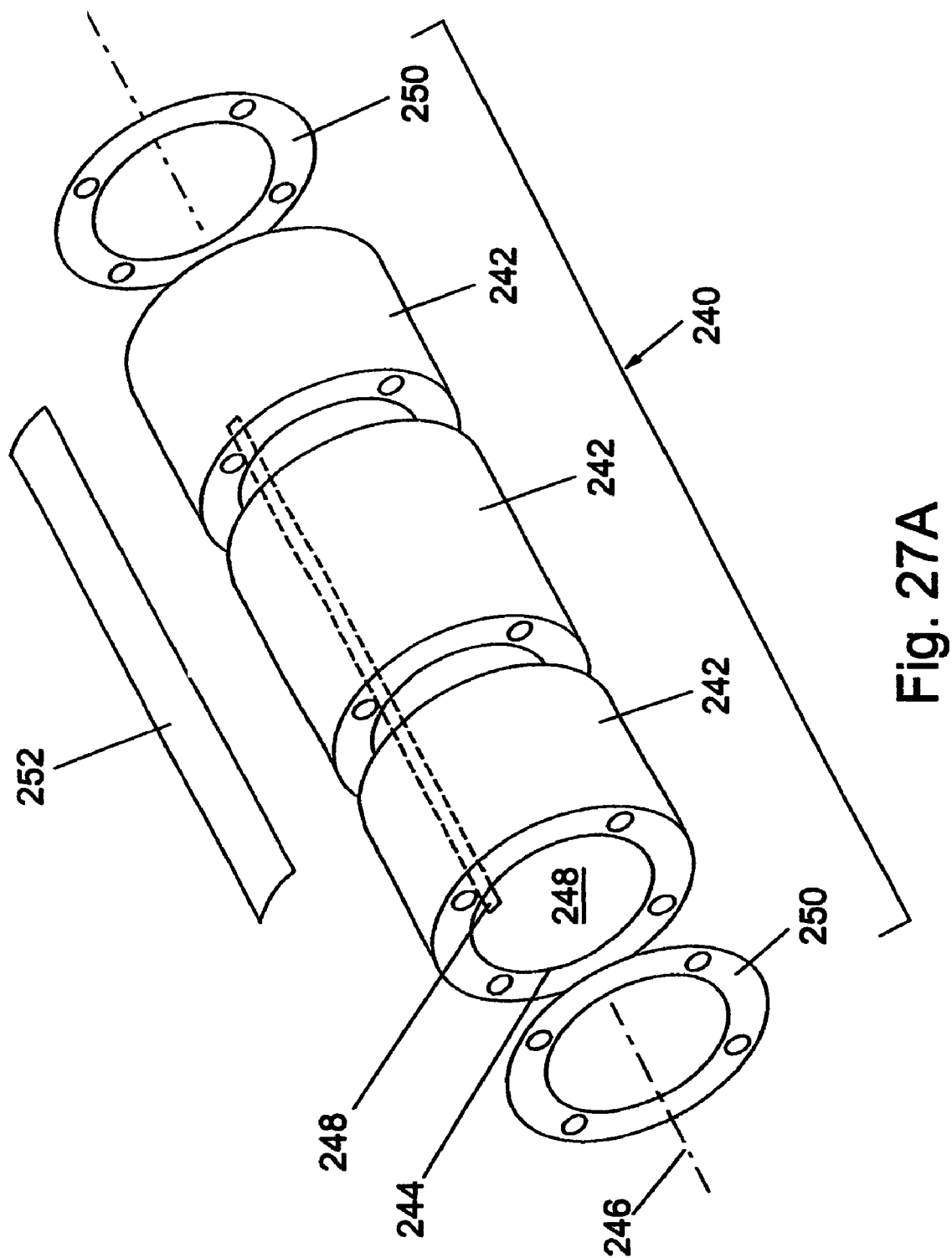
FIG. 27A is an exploded perspective view of an exemplary volume coil.

Referring to FIG. 27A, an exploded perspective view of the volume coil 240 is shown with the core shown in three segments. The volume coil 240 has a cylindrical non-metal core module 242. The core module 242 has a cylindrical bore 244 that extends through the core module 242 along a longitudinal axis 246. The cylindrical bore 244 defines an inner surface 248. The volume coil 240 has a plurality of conductive strip lines 248 extending parallel to the longitudinal axis 246 on the inner surface 248 of the core module 242.

Figure 27B:
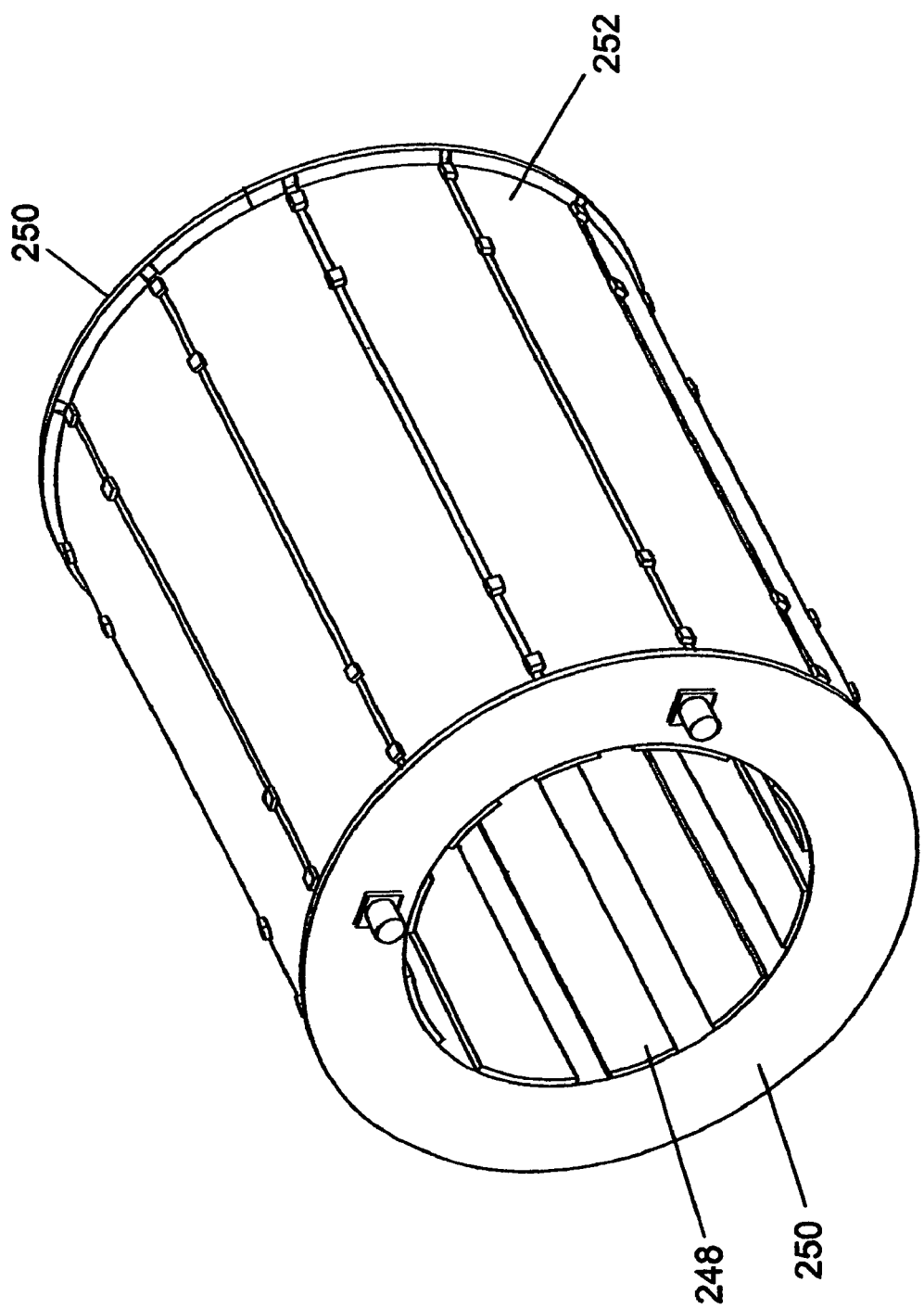
FIG. 27B is a perspective view of an exemplary slotted volume coil.

The volume coil 240 has a pair of printed circuit boards (PCB) 250 mounted on the outer, side edges of the core module 242. In addition, the volume coil 240 has shielding 252 which overlies the core module 242 as seen in FIG. 27B. The shielding 252 is formed in strips to reduce the occurrence of eddy currents induced by the gradient coils. The shielding 252 in strips forms a plurality of coaxial slots along the coil's length which serve to interrupt switched gradient induced eddy current propagation. Reactively bridged azimuthal slots can extend around the TEM coil's outer wall, end walls, and inner "wall" further limit eddies, and extend the coil's frequency band and dimensional options.

In addition to the shielding 252 being strips, the conductive strip lines 248 creates slots that interrupt eddy current propagation in the TEM coil divide the cavity wall, front to back. The inner elements can be flat, copper foil double-sided strip-line elements, split coaxial elements, or single line copper conductors. FIGS. 27A and 27B show copper foil strip line elements for strip lines 248. This segmented TEM coil combines the internal line element 248 with the external cavity segment, the shielding 252, forming a resonance circuit. Each functional element can be sub-divided capacitively into one through four or more segments. Trimmer capacitors on the outside wall of the FIG. 27B coil depict one such division. As in a simple surface coil, the number of capacitive divisions in each resonant unit can be chosen to be few when a more inductive, lower frequency performance of the TEM coil is desired. In contrast, each unit can be divided four or more times to affect the resonance frequency of this slotted TEM volume coil. The rotating magnetic field generated by this subdivided coil will have improved field linearity and homogeneity since the coil is electrically modified.

The printed circuit board 250 shown in FIG. 28A is an exposed surface 262, the surface of which faces away from the core module 242 of the volume coil 240. While FIG. 28B shows the inner surface, the surface which faces the core module 242. The inner surface which is covered with and is part of the shielding along with strips of shielding 252 shown in FIGS. 27A and 27B. The printed circuit board 250 has a plurality of components which are discussed with respect to FIGS. 29-32B.

Figure 29:
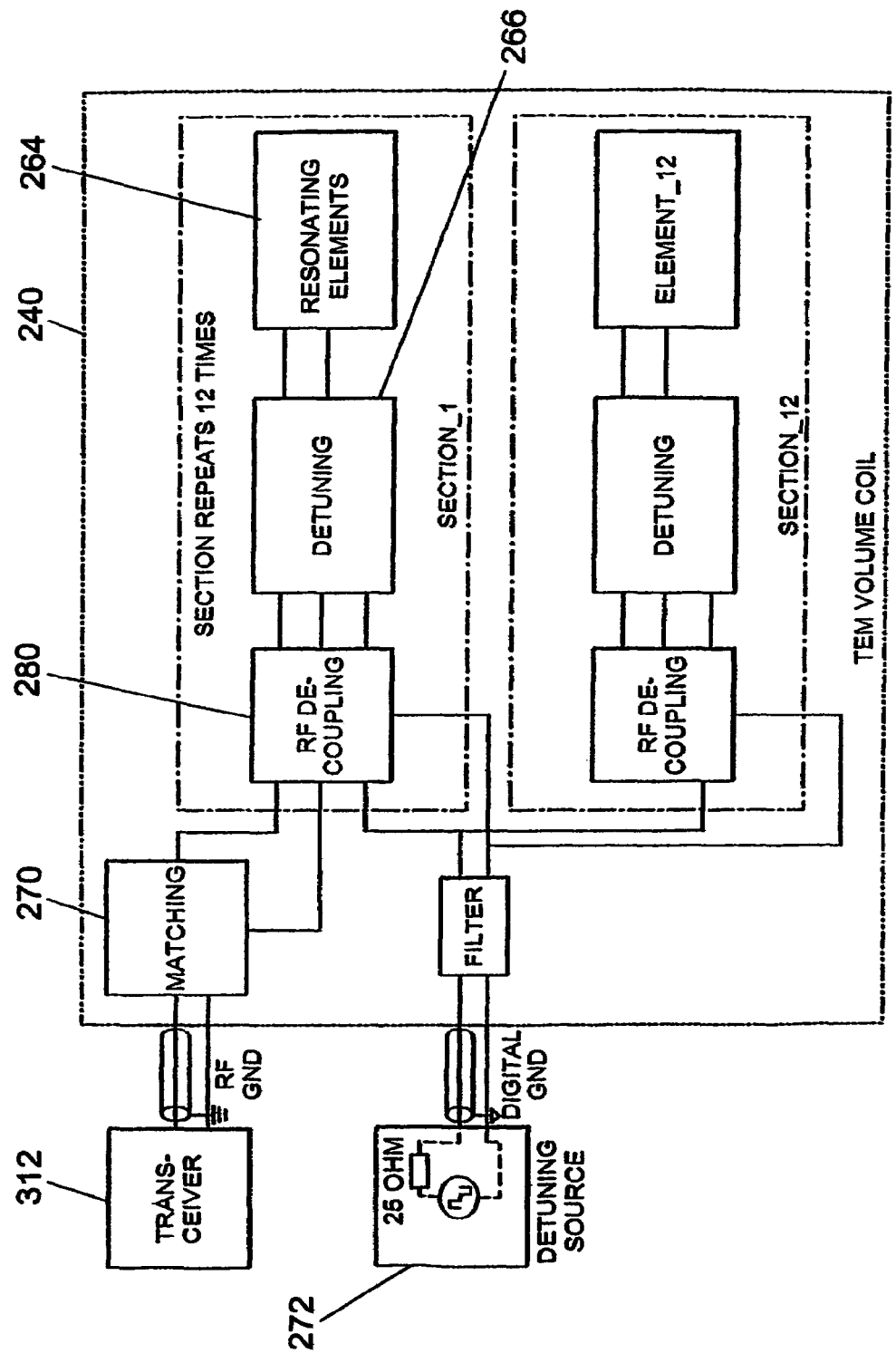
FIG. 29 is a schematic of circuitry associated with the volume coil.

A schematic of circuitry associated with the volume coil 240 is shown in FIG. 12. The volume coil 240 has a plurality of resonating elements 264 which include the strip lines 248 and the shielding 252 (FIGS. 27A and 27B). The elements 264 represented as number 1 and number 12 of a twelve element volume coil 240 are shown. It is recognized that the TEM volume coil 240 can have more or fewer elements 264, such as 8 or 16. The resonating elements 264 are connected to a detuning/tuning circuits 266 in order to move the resonance frequency of the resonating elements 264 away from the target resonance so as not to interfere with the receiving coil as explained in further detail below. The volume coil 240 in addition has a matching circuit 270 for adjusting the impedance of the resonating element 264 to that of the RF source. The TEM volume coil 240 is shown in FIG. 29 with the transceiver unit 312 and a detuning source 272 associated with its circuitry. The RF source 274, the transceiver unit 312 and the detuning source 272; however, are not part of and are located remote from the volume coil 240 and are connected through coaxial cables which connect to the transceiver unit 312. The volume coil 240 has an RF decoupling circuit 280. The RF decoupling circuit 280 ensures that the DC detuning signal does not interfere with the RF signal path.

Figure 30:
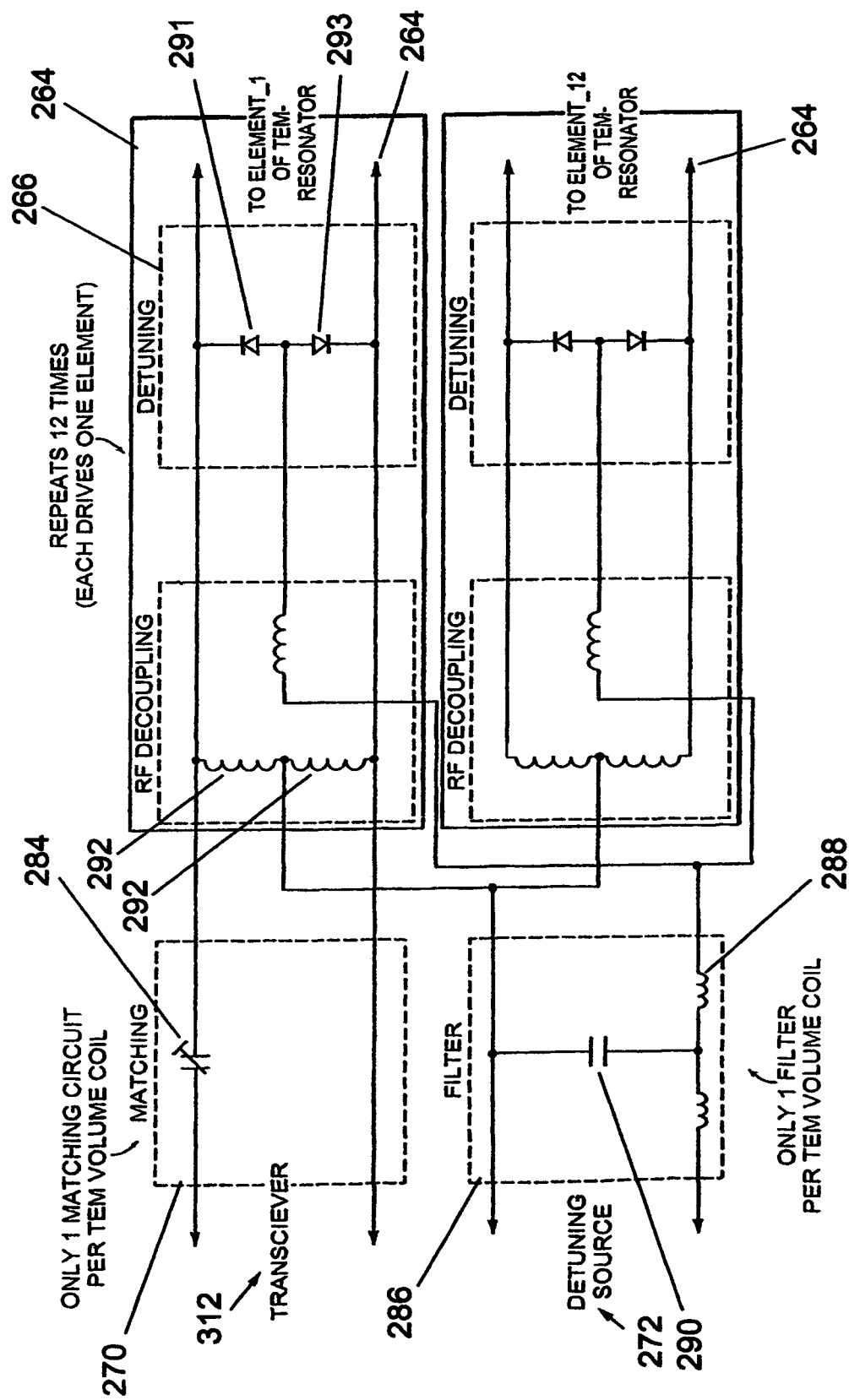
FIG. 30 is a schematic of a circuitry system on the volume coil.

FIG. 30 shows a more detail view of circuitry associated with the volume coil 240 located on the volume coil 240. The matching circuit 282 includes a variable tunable capacitor 284. The detuning source 272 is connected to the detuning circuit 266 via a filter circuit 286 and the RF decoupling circuit 280. The filter circuit 286 has a pair of inductors 288 and a capacitor 290. The filter 286 is for separating the high frequency RF from interfering with the tuning/detuning signal. The RF decoupling circuit 280 has three radio-frequency chokes (RFC) 292 which represent low resistance to the DC current, but high impedance to the RF signal, thereby decoupling both signals from each other. From the detuning circuit 266 which contains either a single pin diode or a pair of pin diodes 291 and 293, the resonating element 264 is connected. If a single diode 291 is employed, then diode 293 is replaced with a short circuit. The benefit of a dual pin diode configuration relates to the fact that if the volume coil is operated in transmit and receive mode, no active DC signal has to be applied.

Figure 31:
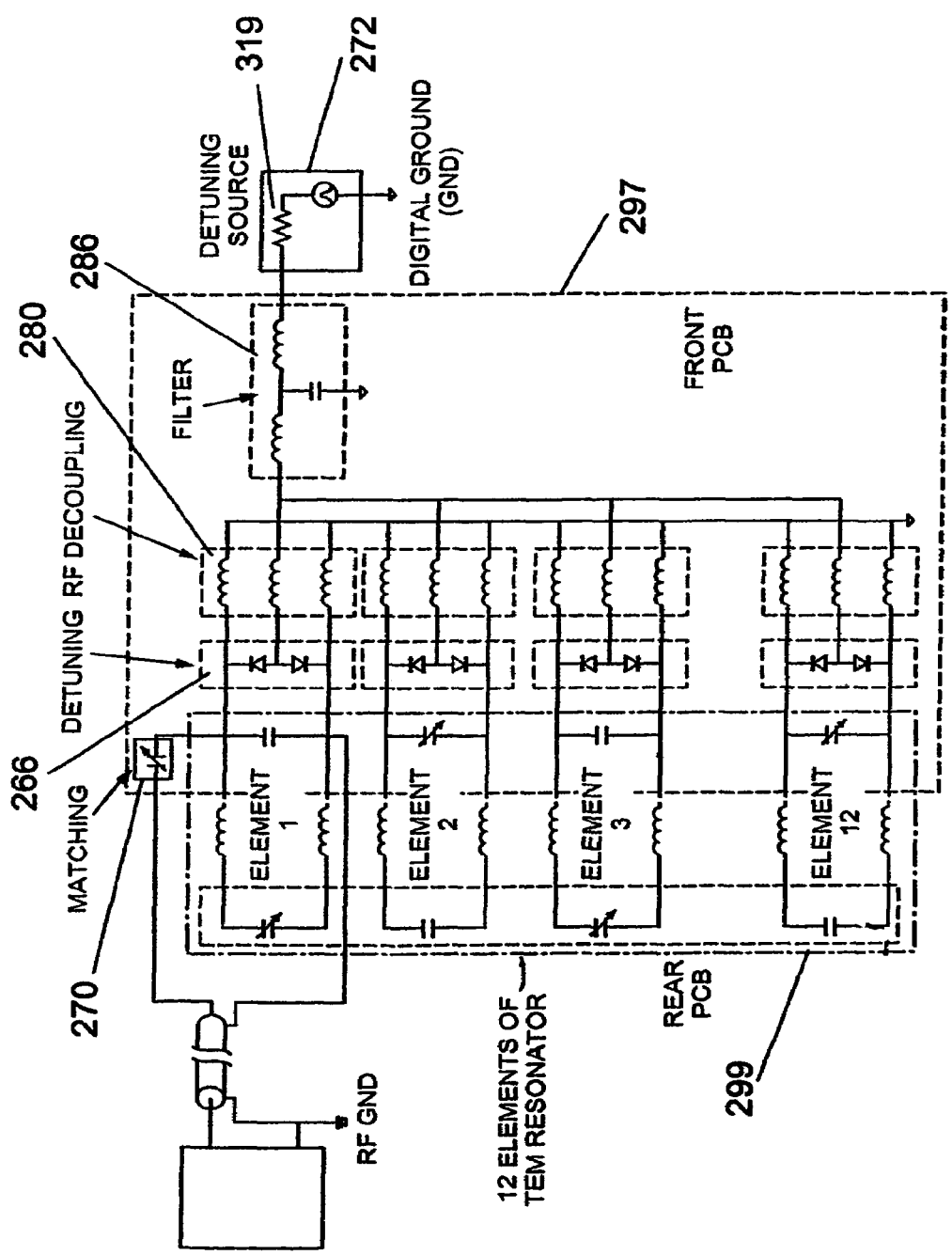
FIG. 31 is a schematic representation of circuitry associated with the volume coil.

FIG. 31 shows additional elements of the circuitry of volume coil 240. As indicated above, the volume coil 240 has several inputs including the RF source 274 from the RF transmitter 316 of the transceiver unit 312, the DC source and a ground. The strip lines 248 are each part of a resonating element 264. The strip lines 248 are represented in the circuit as distributed inductor in the resonating element. The strip lines 248, as represented by the inductors, are connected in series to a pair of capacitors 253 and 255 (FIGS. 31-32B). One of the capacitors is the variable, tuneable capacitor 255. In the embodiment shown in FIG. 31, the variable, tuneable capacitors 255 of one of the resonating element 264 is located on the front PCB 250 and the variable, tuneable capacitors 255 of the adjacent resonating elements are located on the rear PCB 250; in that there are an even number of resonating elements, the variable, tuneable capacitors 255 are equally located on the front PCB and the rear PCB. The other capacitor, the capacitor 253, for each resonating element is located on the other PCB 250 than that of the variable, tuneable capacitor 255.

In an alternative embodiment, all the variable, tuneable capacitors 255 of the resonating elements 264 are located on the front PCB 250. The other capacitor, the capacitor 253, is located on the rear PCB 250. The front PCB 250 is represented by boxes 297 in FIG. 31 and the rear PCB 250 is represented by boxes 299. The strips of shielding 248 are represented by a distributed inductor. The variable, tuneable capacitors 255 can be tuned manually or electronically. An electronically tuneable capacitor can be implemented by replacing capacitor 255 with a so-called varactor diode whose capacitance changes as a function of applied bias voltage. The capacitors 253 and 255 are each carried on the printed circuit board 250. One of the sets of the capacitors 253 and 255 and a strip line 248 in conjunction with the outer strip shielding 248 form an element which is connected to the detuning circuit 266.

Each of the detuning circuits 266 has a pair of diodes 291 and 293. In one embodiment, the diodes 291 and 293 are pin diodes. The RF decoupling circuit 280 has a plurality of inductors 292. One of the detuning circuits 266 and one of the decoupling circuits 280 are each interposed between one of the resonating elements 264 and the filter circuit. The filter 286 is connected to the DC source 272 through a resistor 319. The DC source 272 is used in operating the circuit in conjunction with surface coil 300 as explained below. Still referring to FIG. 31, the RF source 274 and the matching circuit 270 are connected to one of the resonating element 264. The matching circuit 270 includes the variable tuneable capacitor 284 which is tuned manually.

Figure 32A:
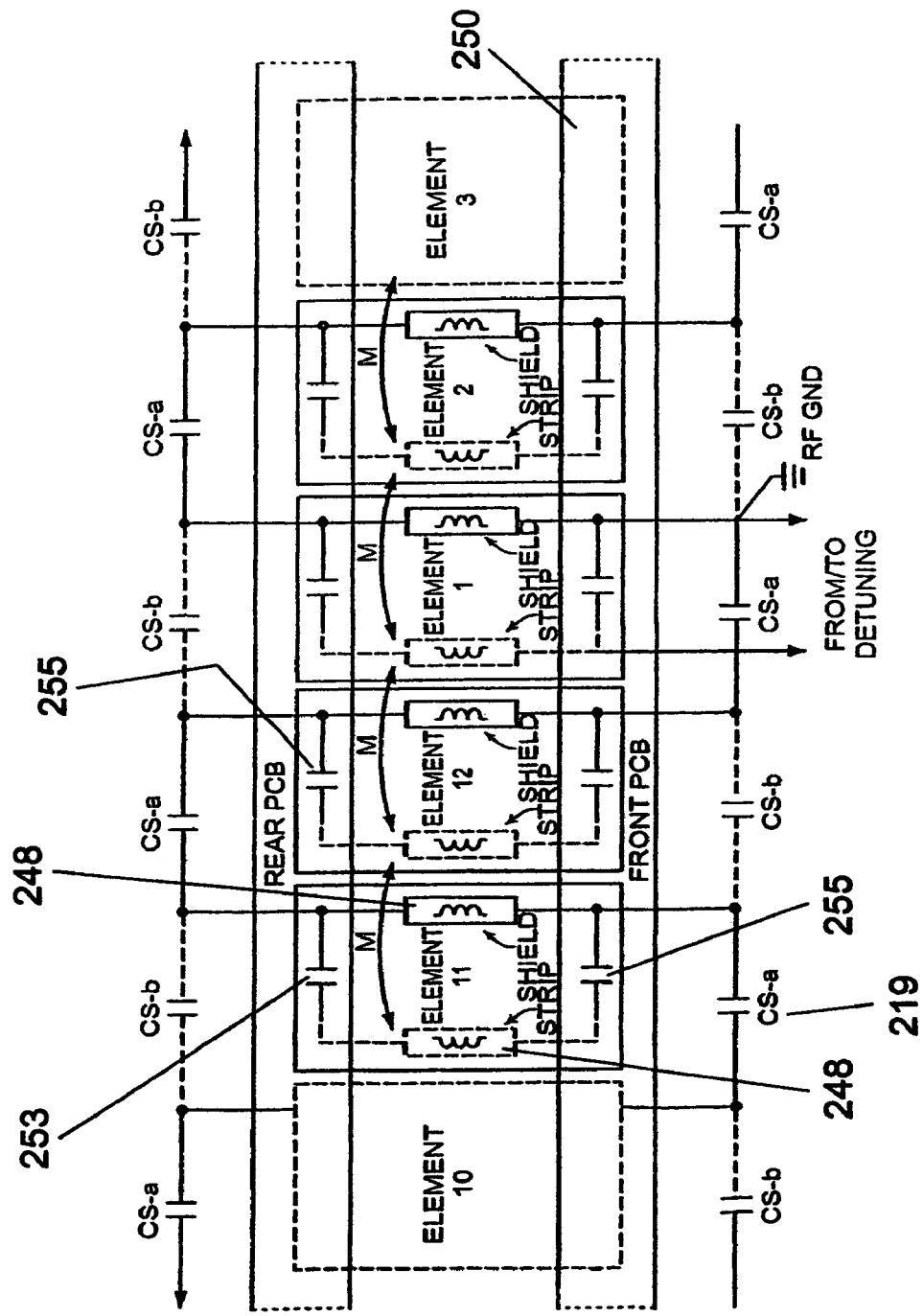
FIG. 32A is a schematic of the conductor circuitry of the volume coil.
Figure 32B:
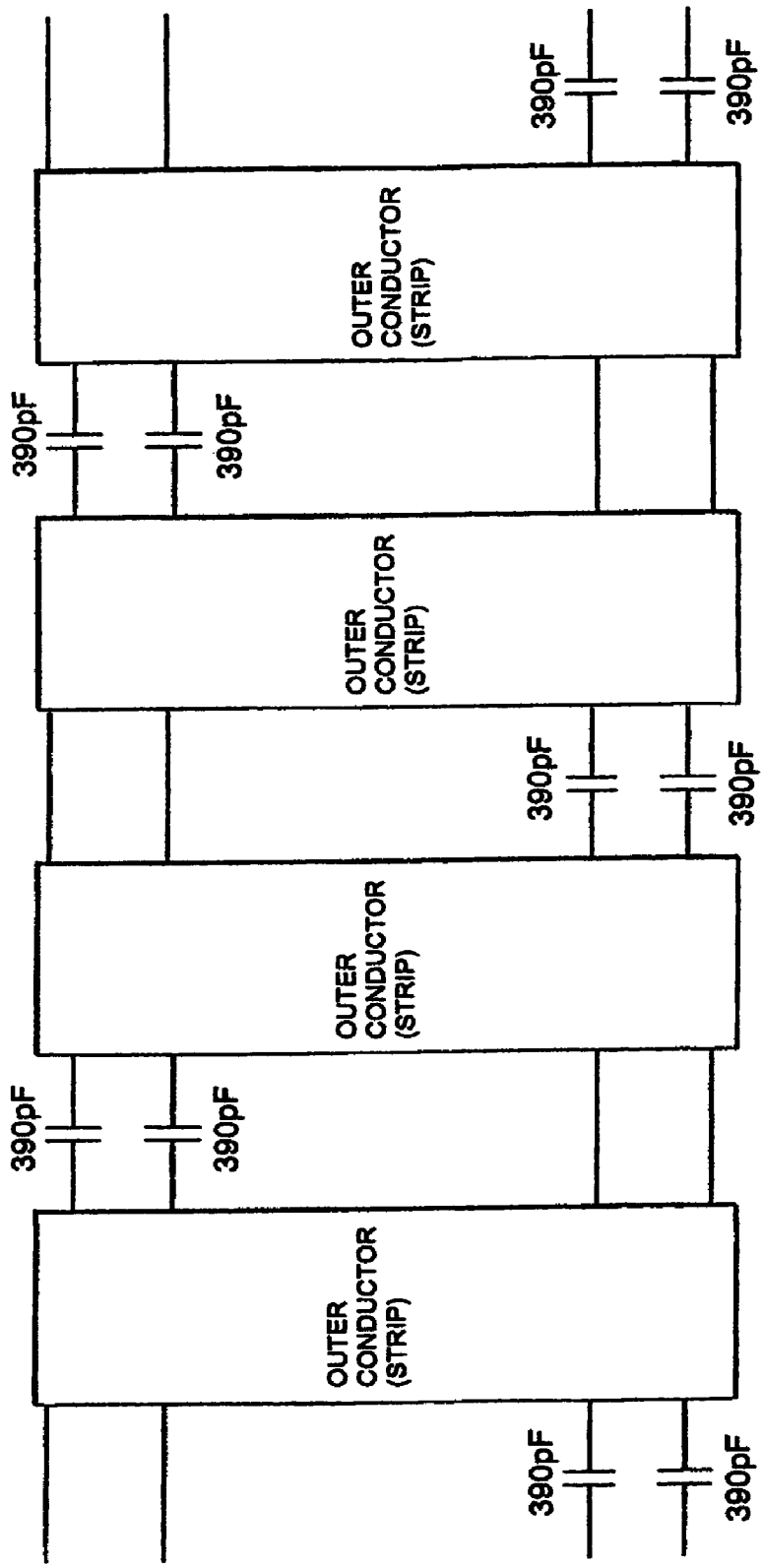
FIG. 32B is a schematic of interrelation of several of the strip of shielding.

Referring to FIG. 32A, a portion of the volume coil 240 is represented. In the embodiment represented in FIG. 32A, twelve elements are located on the volume coil 240. The strip lines 248 are represented by distributed inductors. Connected to the strip line 248 is a pair of capacitors in the series 253 and 255 wherein one of the capacitors 255 is a variable tuneable capacitor. In the embodiment shown in FIG. 32A, the variable, tunable capacitors 255 is shown alternating from being on the front printed circuit board 250 to being on the rear printed circuit board 250 for every other resonating element. In addition, each element shows the shielding 248 which is the return path for the respected strip line 248. The adjacent strip lines 248 are mutually coupled.

As indicated above, the volume coil 240 has shielding 248 located on the outer surface of the core module 242. The strips of shielding 248 are connected to each other by capacitors located at alternative ends of the strips of shielding 248. The capacitors 219 are located on the outer surface of the resonating element as part of the shielding 248. Additional capacitors may be located at the other end of the strips of shielding 248 or alternatively they may be shorted in an effort to reduce the occurrence of eddy currents due to the activation of the gradient coils. The first element shown connected to a detuning circuit. A schematic showing the connection of adjacent strips of shielding 248 for a portion of the volume coil 240 is seen in FIG. 32B. The strips of shielding 248 are connected to each other by capacitors located on the outer surface of the resonating element as part of the shielding such as seen in FIG. 27B. The capacitors are located at alternative ends of the strips of shielding 248. In the embodiment shown, the other end of the strips of shielding 248 are shorted to reduce the occurrence of eddy currents as discussed above.

Working with the volume coil 240 is the surface coil 300 that can be used in one mode to receive the MR signal from the animal. In another mode, the surface coil 300 both transmits and receives the RF signal.

Figure 33A:
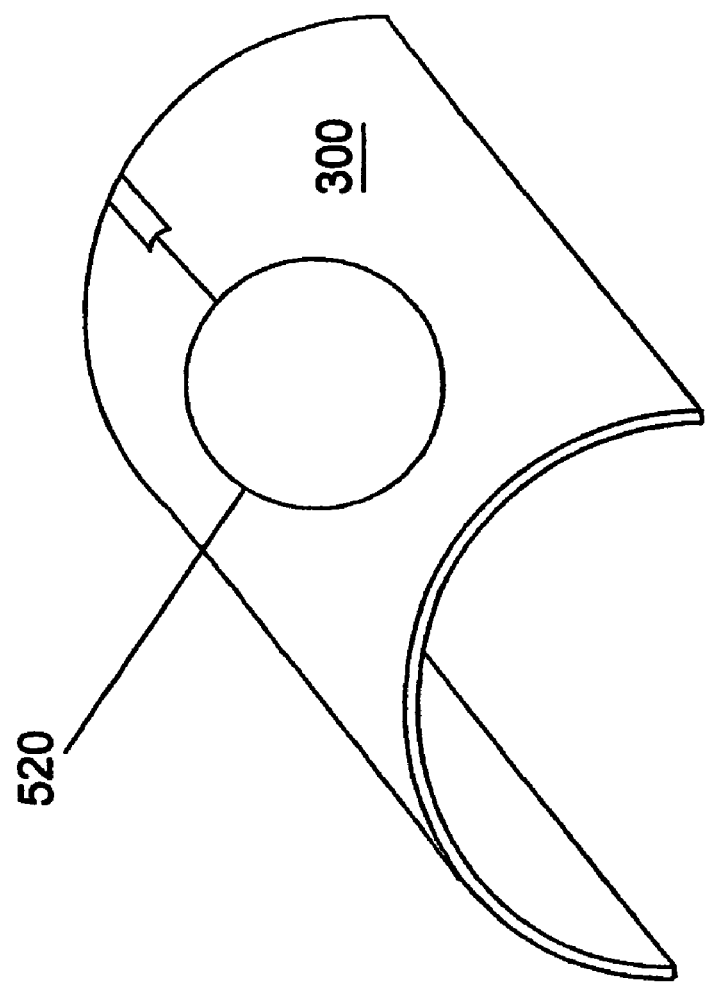
FIG. 33A is a view of a single loop surface coil.
Figure 33B:
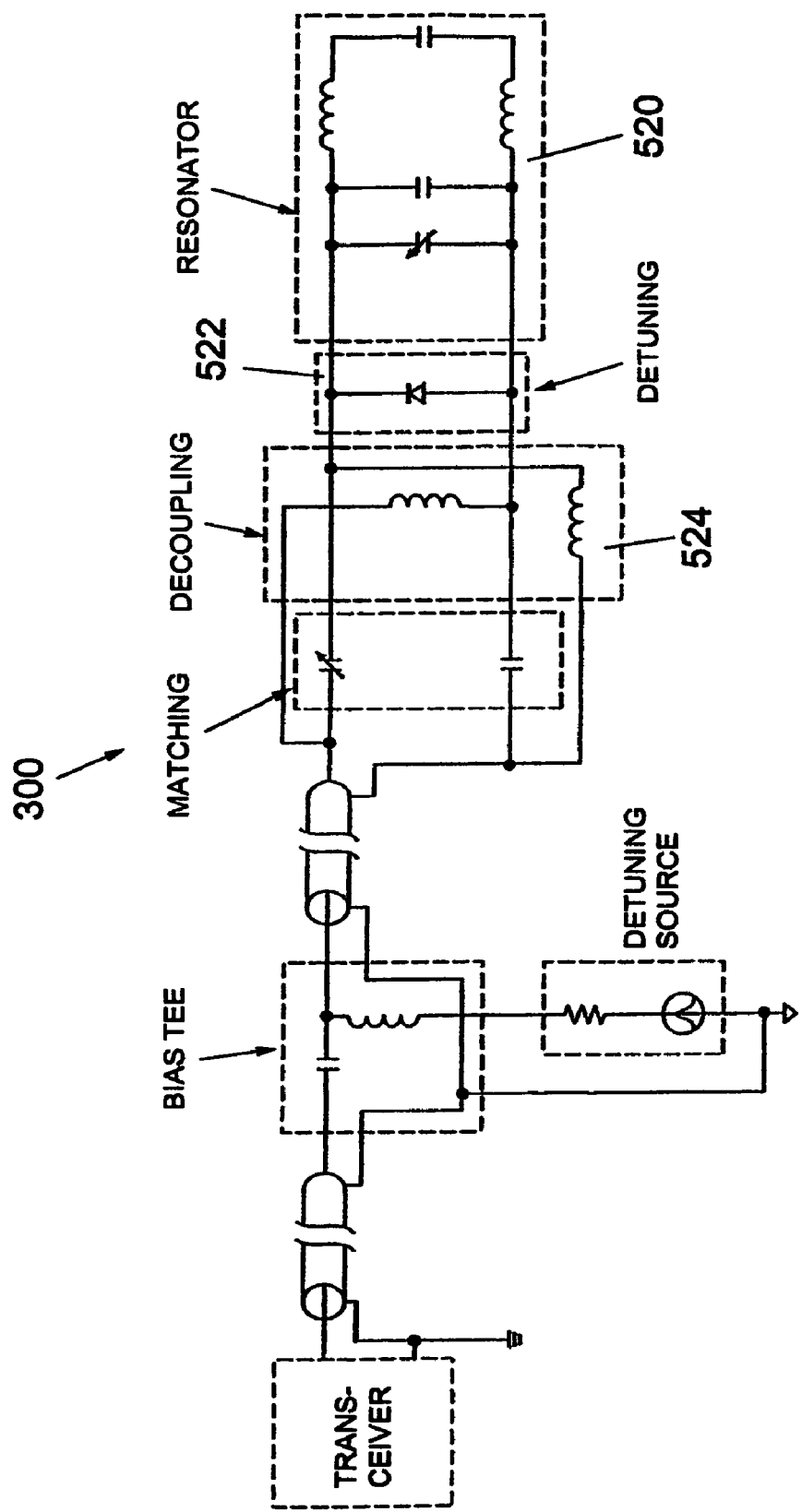
FIG. 33B is a schematic circuit of a single loop surface coil.
Figure 34A:
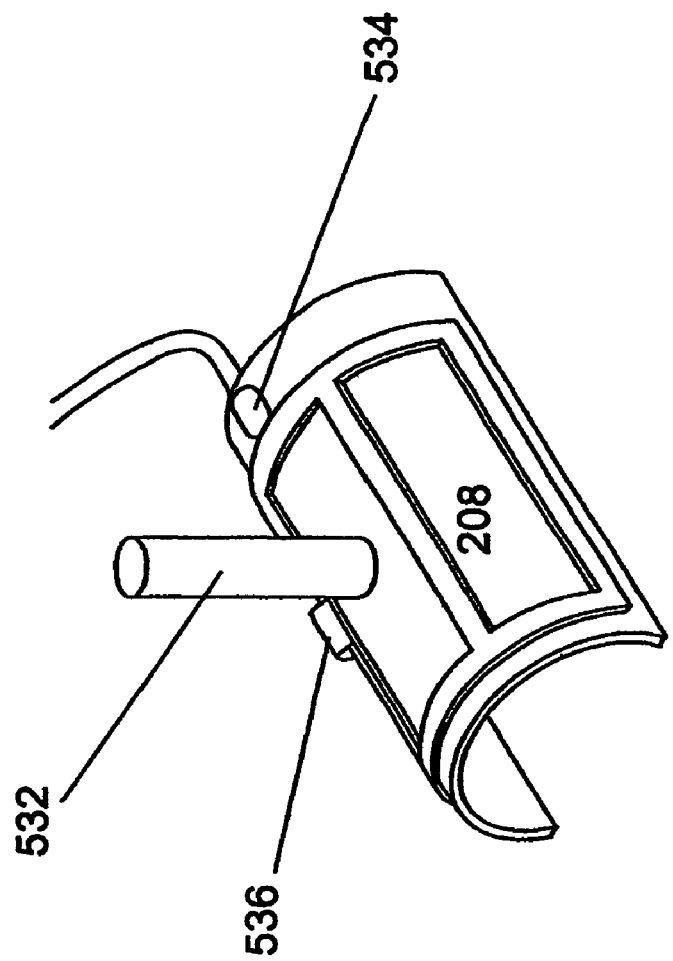
FIG. 34A is a view of a dome shaped surface coil.
Figure 34B:
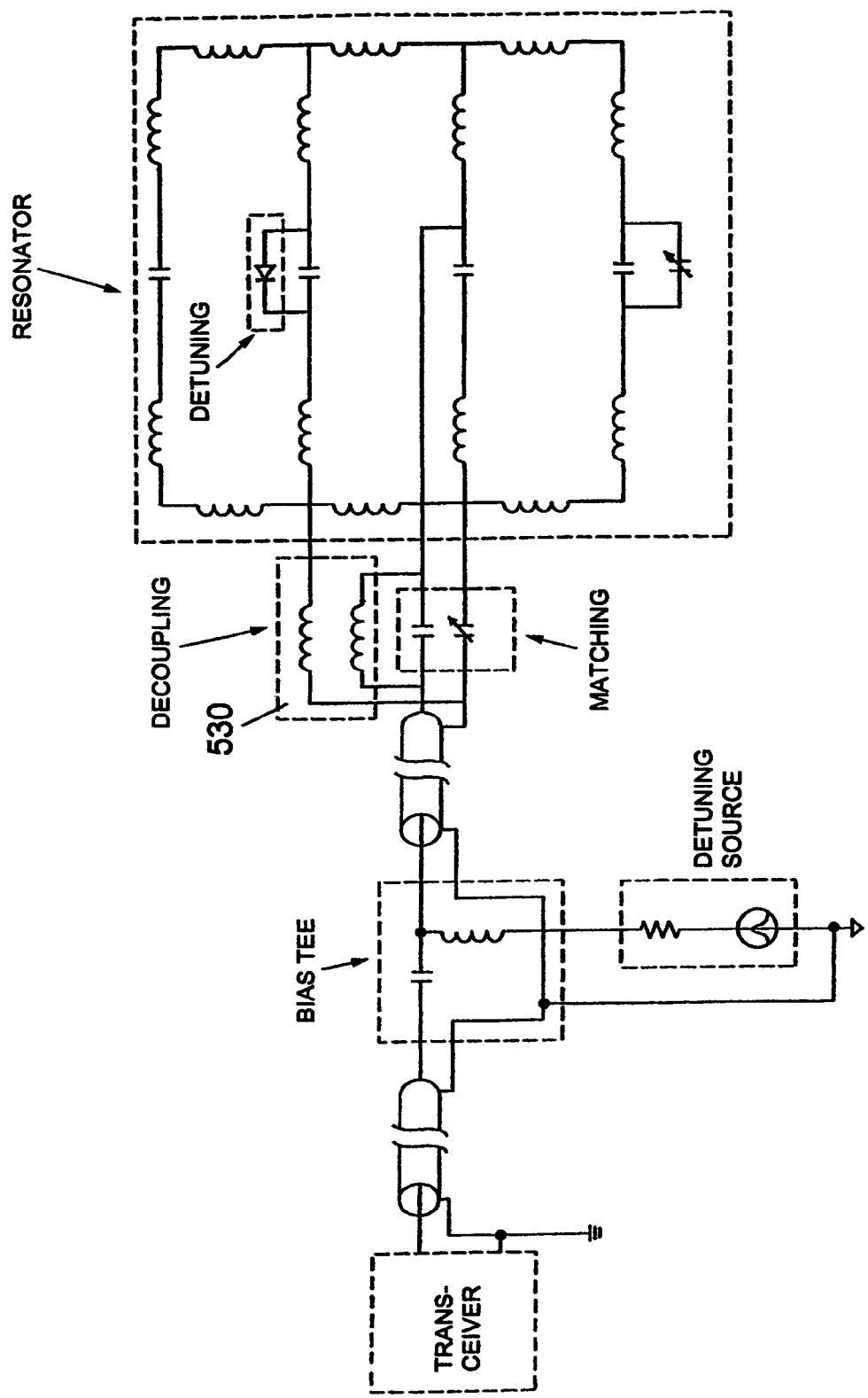
FIG. 34B is a schematic of circuitry of a dome surface coil.

It will be appreciated that the above description of the volume coil 240 and its related hardware is provided to give only a brief overview thereof and additional details are set forth in U.S. patent application Ser. No. 09/694,087, which is hereby incorporated by reference in its entirety. Accordingly, it is understood, that other volume coil constructions can be equally applicable and suitable The surface coil 300 can take various shapes. The surface coil 300 can have a single loop as described with respect to FIGS. 33A-33B or have multiple loops arranged in a dome shaped surface coil 530 as seen in FIGS. 34A-34B. Referring to FIGS. 33A and 33B, the surface coil 300 with a single loop is shown. The circuitry of the surface coil 300 of FIG. 33A is shown in FIG. 33B. A resonating element 520 of the single loop has a pair of metallic strips with interposed capacitors schematically shown in FIG. 33B. The single loop surface coil 300 has a detuning circuit 522 and a decoupling circuit 524. The single loop surface coil 300 has a connection to the transceiver and the detuning source. The single loop surface coil 300 preferably includes a post for attaching to the head holder 400 or another device. An alternative to the single loop surface coil 300 of FIGS. 33A and 33B is a multiple loop dome shaped surface coil device 530 illustrated in FIG. 34A. FIG. 34B is a schematic of the multiple loop surface coil device 530. The surface coil 530 preferably has a post 532 as seen in FIG. 34A for attaching to the head holder 400 or another device. The surface coil 530 includes a pair of connectors 534, 536 which are connected to the RF source and the DC source. Similar to the volume coil 240, the surface coil 530 has a detuning circuit 538 and matching capacitor circuit 540. Also similar to the volume circuit 240, the surface coil 530 has the inputs of the RF source, the DC source and the ground. The surface coil 530 has a plurality of resonating elements 542 each with a strip line which is represented by an inductor. Both fixed and tuneable capacitors are deployed. The tuneable capacitor is used to adjust the resonance frequency with a capacitor being used to match the circuit. Other details of exemplary surface coils are set forth in the previously-incorporated U.S. patent application Ser. No. 09/694,087.

The animal (e.g., monkey) can be lightly anesthetized prior to insertion into the restrainer 100. A semi-circular ear piece (not shown) is fitted over the head of the monkey and then the monkey's head is inserted into the head holder 400. Lateral ear clamping screws (not shown) are inserted through the pair of slots 420 and tightened against divots in the semi-circular ear piece to prevent the monkey from moving horizontally. The animal's chin is placed within the contoured chin holder part 720, which serves to restrict the movement of the monkey's chin region when it is held within the restrainer 100. The hands of the monkey are inserted between the arm holder parts such that the arms of the monkey are disposed within the openings such that the fingers of the monkey extend below the arm holder 600. As previously mentioned, the left and right arm pieces 800, 900 are preferably inserted into these same openings so as to further immobilize the monkey's arms; however, the fingers of the monkey remain free.

The chest region of the animal is restrained between the pair of adjustable chest holders 220 such that the second sections 224 of the holders 220 are brought into snug contact with the chest of the animal. As previously mentioned, the chest holders 220 are adjustable across the platform 160 and are secured in selected positions by passing fasteners through the slots 226 and the corresponding openings formed in the platform 160. In the restrained position, the lower half of the monkey extends across the ramp structure 170, with the knees extending into the openings 169. The lower portions of the monkey's legs are restrained in position using the leg holder 500. The leg holder 500 is adjustably restrained relative to the ramp structure 170 by first finding the desired position of the leg holder 500 with respect to the animal's feet (e.g., the leg holder 500 should be located in the ankle region) and then inserting fasteners through the openings 510 and 151 to effectively retain the leg holder 500 on the ramp structure 170. The hip holder 430 is adjusted in the manner previously mentioned so that it applies a force to the buttocks and hip areas of the animal when the cover 180 is closed. All of the aforementioned components of the restrainer 100 ensure that the animal is securely restrained within the restrainer 100.

The present restrainer construction not only provided benefits due to it being a dual coil design but also it is configured so that the animal (e.g., _____ monkey) is restrained at a number of different body locations so as to greatly restrict the movement of the animal within the restrainer assembly. This directly results in an elimination or substantial reduction in the motion artifacts phenomena that plagues the prior art systems.

While this invention has been particularly shown and described with references to preferred embodiments thereof, it will be understood by those skilled in the art that various changes in form and details may be made therein without departing from the scope of the invention encompassed by the appended claims.

What is claimed is:

1. A restraining assembly for an awake animal within a magnetic resonance imaging (MRI) device, the restraining assembly comprising: a body restrainer having a first part and a second part that hold a body of the awake animal therebetween; a volume coil for generating an excitation RF signal, the volume coil being removably coupled to a holder that is securely coupled to the body restrainer; an RF surface coil for receiving an RF response from the animal, the RF surface coil being carried by a component that is disposed within the volume coil; and an adjustable hip holder that has a first section that seats against and applies a restraining force to a buttocks/hip area of the animal and a second section that is adjustably coupled to a pivoting member that is attached to the first part of the body restrainer such that the hip holder is adjustable in both a longitudinal direction along a length of the body restrainer and is pivotally adjustable in an up/down direction within the body restrainer between the first and second parts thereof, the first part of the body restrainer comprises a cover and the body restrainer further comprises a connector plate attached to the second part of the body restrainer, the connector plat having a flange member, one end of the first part seating against the flange member when the first and second parts are in a closed position, the connector plate having an opening formed thererthrough for receiving the head of the animal, the pivoting member having features that permit the hip holder to be locked in a desired location both in the longitudinal direction and the up/down direction so that a sufficient restraining force is applied the animal.

2. The restraining assembly of claim 1, wherein the volume coil includes a cylindrical non-magnetic core module having an outer shield and a longitudinal axis, a cylindrical bore extending through the core module along the longitudinal axis and defining an inner surface.

3. The restraining assembly of claim 1, wherein the second part is a generally hemi-spherical body and the first part is a generally hemi-spherical cover that is pivotally coupled to the second part, the cover having a length that is less than a length of the second part of the body restrainer.

4. The restraining assembly of claim 3, wherein the volume coil is disposed between the connector plate and one end of the second section that does not include the first section.

5. The restraining assembly of claim 1, wherein the second section includes a raised platform for receiving a chest region of the animal and a sloped ramp that joins one end of the platform and receives lower extremities of the animal, the ramp being sloped down toward one end of the second section opposite an end that receives the volume coil, the ramp terminating prior to an end of the second section of the body restrainer.

6. The restraining assembly of claim 5, wherein the sloped ramp has a pair of openings formed therein for receiving the knees of the animal when the animal is restrained within the body restrainer.

7. The restraining assembly of claim 1, further comprising: a head holder having an opening formed therethrough for receiving and restraining the head of the animal, the surface coil being disposed within the head holder.

8. The restraining assembly of claim 1, wherein the second section of the hip holder is an elongated member with the first section of the hip holder joined to the second section at one end thereof, the first section extending outwardly away from the one end of the second section such that a predetermined angle is defined between the first and second sections.

9. The restraining assembly of claim 8, wherein the predetermined angle is less than 90 degrees.

10. The restraining assembly of claim 8, wherein the elongated member has a closed ended slot formed therein and the first and second sections are integrally formed.

11. The restraining assembly of claim 8, wherein the first section has a pair of legs formed at ends thereof and a plurality of curved surfaces for receiving the hips of the animal and seating against the buttocks of the animal such that the animal is restrained between the pair of legs.

12. The restraining assembly of claim 1, further including a pivot base member that is attached to the first part of the body restrainer near or at one end thereof, the base member having a pair of legs that are spaced from one another a sufficient distance so that the pivoting member is received therebetween and is pivotally coupled to the legs.

13. The restraining assembly of claim 12, wherein the pivoting member includes a pair of spaced parallel walls that are connected to one another at first ends thereof by a connecting wall that extends therebetween, the parallel walls including at least one pair of openings that are aligned with each other and with openings formed in the legs of the base member so that a pivot pin can be received therethrough to pivotally couple the pivoting member to the base member.

14. The restraining assembly of claim 13, wherein the parallel walls have a pair of axially aligned slots formed therein that are also axially aligned with openings formed in the legs of the base member for receiving fasteners that lockingly retain the pivoting member in a desired position relative to the base member.

15. The restraining assembly of claim 13, wherein a portion of the second section of the hip holder is disposed against one face of the connecting wall such that an elongated slot formed in the second section of the hip holder is axially aligned with an opening formed through the connecting wall to permit at least one fastener to securely attach the second section of the hip holder to the pivoting member such that the hip holder is prevented from moving in the longitudinal direction.

16. The restraining assembly of claim 1, further including: an arm holder that includes a pair of openings for receiving the hands and a portion of the arms of the animal, the arm holder being mounted to the second section of the body restrainer; and left and right arm pieces that are removably disposed within the respective pair of openings of the arm holder, each arm piece having a body with a lip portion that seats against an upper surface of the arm holder to position the arm piece relative to the arm holder, wherein the body of each arm piece effectively reduces the diameter of the opening to aid in immobilizing the arms of the animal.

17. The restraining assembly of claim 16, wherein each of the arm pieces includes a locking tab for securely attaching the arm piece to the second section of the body restrainer and a tongue that is integral to the body of the arm piece and extends outwardly therefrom, the tongue having a curved face to nest against the arm.

18. The restraining assembly of claim 17, wherein the body of each arm piece includes a flat that is positioned against a side edge of the body section of the body restrainer when the arm piece is inserted into the arm holder.

19. The restraining assembly of claim 1, further including: a chin holder for holding and restraining a chin of the animal, the chin holder having a base section that is removably attached to an arm holder which is itself attached to a part of the body restrainer and a contoured chin holder member that is integrally attached to the base section and has a curved shape to permit the animal's chin to rest therein.

20. The restraining assembly of claim 19, wherein the base section of the chin holder includes a first vertical section, a horizontal section attached to the first vertical section at one end thereof, and a second vertical section that is attached to another end of the horizontal section with the first and second vertical sections extending away from the horizontal sections in opposite directions, the contoured chin holder member being attached to the second vertical section.

21. The restraining assembly of claim 20, wherein the first vertical section has an opening formed therethrough for receiving a fastener to securely attach the chin holder to the arm holder.

22. The restraining assembly of claim 20, wherein the second vertical section has an opening formed therethrough for receiving a locating post that extends outwardly from the arm holder for locating and positioning the chin holder with respect to the arm holder.

23. The restraining assembly of claim 5, further including: a leg holder that is adjustably attached to the sloped ramp for restraining the feet of the animal, the leg holder having a pair of arcuate sections to accommodate the feet of the animal between the leg holder and the sloped ramp.

24. The restraining assembly of claim 23, wherein the leg holder has a base section that is formed between the arcuate sections, the base section having an opening therein for receiving a locking fastener that is received therethrough and into one of a plurality of linearly aligned openings that are formed in the sloped ramp, the leg holder being adjusted by repositioning the base section such that the opening in the base section aligns with a different opening formed in the sloped ramp.

25. A restraining assembly for an awake animal within a magnetic resonance imaging (MRI) device, the restraining assembly comprising: a body restrainer having a cover that is attached to a base for holding a body of the awake animal therebetween and is positionable between an open position and a closed position relative to the base; a volume coil for generating an excitation RF signal, the volume coil being removably coupled to a holder that is securely coupled to the body restrainer; an RF surface coil for receiving an RF response from the animal, the RF surface coil being carried by a component that is disposed within the volume coil; wherein the first part of the body comprises a connector plate attached to the second part of the body restrainer, the conector plate having a flange member, one end of the first part seating against the flange member when the first and second parts are in a closed position, the connector plate having an opening formed therethrough for receiving the head of the animal; and an adjustable hip holder that has a first section that seats against and applies a restraining force to a buttocks/hip area of the animal and a second section that is adjustably coupled to a pivot assembly that pivotally attaches the hip holder to the cover of the restrainer, the pivot assembly having a base member that is attached to an inner surface of the cover and a pivotable member that is pivotally attached to the base member so as to extend downwardly therefrom toward the base when the cover is closed, the second section of the hip holder being pivotally coupled to the pivotable member, wherein the hip holder is adjustable in both a longitudinal direction along a length of the body restrainer and is pivotally adjustable in an up/down direction within the body restrainer between the cover and base thereof.

26. The restraining assembly of claim 25, wherein the hip holder includes an elongated section and a main body at one end of the elongated section, the main body having a pair of arcuate surfaces for seating against a buttocks area, the elongated section being attached to the pivotable member.

27. The restraining assembly of claim 26, wherein the elongated section includes a slot extending along a length thereof and that receives a fastener for attaching the elongated section to the pivotable member, the slot permit longitudinal adjustment of the elongated section relative to the pivotable member until a desired position is reached at which time the fastener is tightened.

28. The restraining assembly of claim 26, wherein the main body includes a slot formed between the pair of arcuate surface for receiving and permitting a tail of the animal to pass through when the hip holder is seated against the animal.

29. The restraining assembly of claim 26, wherein the pivotable member includes a first locking member for locking the elongated section in the longitudinal direction relative to the pivotable member and a second locking feature for locking the elongated section in the up/down direction relative to the pivotable member such that when the cover is shut relative to the base, the hip holder is locking in a predetermined position such that pressure is applied to the buttocks and hips of the animal.

30. The restraining assembly of claim 25, wherein the cover is hingedly connected to the base.

* * * * *